(12) United States Patent
Burstein et al.

(10) Patent No.: US 7,544,714 B2
(45) Date of Patent: Jun. 9, 2009

(54) LIPID-AMINO ACID CONJUGATES AND METHODS OF USE

(75) Inventors: Sumner H. Burstein, Framingham, MA (US); Robert B. Zurier, Princeton, MA (US)

(73) Assignee: University of Massachusetts, Boston, MA (US)

( * ) Notice: Subject to any disclaimer, the term of this patent is extended or adjusted under 35 U.S.C. 154(b) by 213 days.

(21) Appl. No.: 11/183,055

(22) Filed: Jul. 15, 2005

(65) Prior Publication Data

US 2006/0014820 A1 Jan. 19, 2006

Related U.S. Application Data

(60) Provisional application No. 60/588,697, filed on Jul. 16, 2004.

(51) Int. Cl.
*A61K 31/20* (2006.01)
*C07D 207/00* (2006.01)

(52) U.S. Cl. .................. 514/558; 514/423; 514/563; 548/537; 554/42; 554/59

(58) Field of Classification Search .......... 514/423, 514/558, 563; 548/537; 554/42, 59
See application file for complete search history.

(56) References Cited

U.S. PATENT DOCUMENTS

| | | | |
|---|---|---|---|
| 3,711,602 A | | 1/1973 | Herschler |
| 4,362,716 A | * | 12/1982 | Bouchaudon et al. ......... 514/19 |
| 4,649,147 A | | 3/1987 | Mueller et al. |
| 4,847,290 A | | 7/1989 | Burstein |
| 4,973,603 A | | 11/1990 | Burstein |
| 5,112,863 A | | 5/1992 | Hashimoto et al. |
| 5,164,414 A | | 11/1992 | Vincent et al. |
| 5,338,753 A | | 8/1994 | Burstein et al. |
| 5,538,993 A | | 7/1996 | Mechoulam et al. |
| 5,635,530 A | | 6/1997 | Mechoulam et al. |
| 5,998,476 A | | 12/1999 | Sleigh et al. |
| 6,162,829 A | | 12/2000 | Burstein |
| 6,262,119 B1 | | 7/2001 | Ferrante et al. |
| 2003/0022938 A1 | * | 1/2003 | Burstein et al. ............. 514/558 |

FOREIGN PATENT DOCUMENTS

| | | |
|---|---|---|
| WO | WO 96/13507 | 5/1996 |
| WO | WO 03/007876 | 1/2003 |
| WO | WO 03/227876 | 1/2003 |
| WO | WO 03/035023 | 5/2003 |
| WO | WO 2006/010153 | 1/2006 |

OTHER PUBLICATIONS

Sleigh et al., 1996, CAS: 125:115138.*
Mueller et al., 1987, CAS: 87:16967.*
Brnier et al., 2003, C2003-146818.*
Hunag et al., The journal of Biological Chemistry, 2001, 276(46): 42639-42644.*

Cascio et al., Biochemical and Biophysical Research Communications, January issue, 2004, 314:192-196.*
Arioglu et al., "Efficacy and Safety of Troglitazone in the Treatment of Lipodystrophy Syndromes," *Ann. Intern. Med.*, 133(4):263-274 (2000).
Asada et al., "Antiinflammatory roles of peroxisome proliferator-activated receptor gamma in human alveolar macrophages," *Am. J. Respir. Crit. Care Med.*, 162(2):195-200 (2004).
Batrakov et al., "The polar-lipid composition of the sphingolipid-producing bacterium *Flectobacillus major*," *Biochim. Biophys. Acta.*, 1484(2-3):225-240 (2000).
Burstein, "The cannabinoid acids: nonpsychoactive derivatives with therapeutic potential," *Pharmacol. Ther.*, 81(1):87-96 (1999).
Burstein et al., "Antagonism to the Actions of Platelet Activating Factor by a Nonpsychoactive Cannabinoid," *J. Pharmacol. Exp. Ther.*, 251(2):531-535 (1989).
Burstein et al., "Oxidative metabolism of anandamide," *Prostaglandins Other Lipid Mediat.*, 61:29-41 (2000).
Burstein et al., "Potential anti-inflammatory actions of the elmiric (lipoamino) acids," *Bioorganic & Medicinal Chem.*, 15:3345-3355 (2007).
Burstein et al., "Regulation of anandamide tissue levels by N-arachidonylglycine," *Biochem. Pharmacol.*, 64(7):1147-1150 (2002).
Cascio et al., "A structure-activity relationship study on N-arachidonoyl-amino acids as possible endogenous inhibitors of fatty acid amide hydrolase," *Biochem. Biophys. Res. Commun.*, 314(1):192-196 (2004).
Clark et al., "The Nuclear Receptor PPARγ and Immunoregulation: PPARγ Mediates Inhibition of Helper T Cell Responses," *J. Immunol.*, 164:1364-1371 (2000).
Cuzzocrea et al., "The cyclopentenone prostaglandin 15-deoxy$\Delta^{12,14}$-prostaglandin $J_2$ attenuates the development of acute and chronic inflammation," *Mol. Pharmacol.*, 61(5):997-1007 (2002).
Forman et al., "15-Deoxy-$\Delta^{12,14}$-Prostaglandin $J_2$ Is a Ligand for the Adipocyte Determination Factor PPARγ," *Cell*, 83(5):803-812 (1995).
Gilroy et al., "Inducible cyclooxygenase-derived 15deoxy $\Delta^{12,14}$PGJ$_2$ brings about acute inflammatory resolution in rat pleurisy by inducing neutrophil and macrophage apoptosis," *FASEB J.*, 17(15):2269-2271 (2003).
Gilroy et al., "New insights into the role of COX 2 in inflammation," *J. Mol. Med.*, 78(3):121-129 (2000).
Hadigan et al., "Metabolic Effects of Rosiglitazone in HIV Lipodystrophy: A Randomized, Controlled Trial," *Ann. Intern. Med.*, 140(10):786-794 (2004).

(Continued)

*Primary Examiner*—Rei-tsang Shiao
(74) *Attorney, Agent, or Firm*—Fish & Richardson P.C.

(57) ABSTRACT

N-fatty acid-amino acid conjugates and $J_2$ prostanoid-amino acid conjugates are disclosed along with methods for making such conjugates and methods of using these conjugates in the treatment of conditions that involve dysfunctional lipid metabolism, insulin sensitivity, glucose homeostasis, and/or inflammation.

17 Claims, 7 Drawing Sheets

OTHER PUBLICATIONS

Huang et al., "Identification of a New Class of Molecules, the Arachidonyl Amino Acids, and Characterization of One Member That Inhibits Pain," *J. Biol. Chem.*, 276(46):42639-42644 (2001).

Jiang et al., "PPAR-γ agonists inhibit production of monocyte inflammatory cytokines," *Nature*, 391(6662):82-86 (1998).

Kawahito et al., "15-deoxy-$\Delta^{12,14}$-PGJ$_2$ induces synoviocyte apoptosis and suppresses adjuvant-induced arthritis in rats," *J. Clin. Invest.*, 106(2):189-197 (2000).

Kawai et al., "Lipoamino acids which are similar to bacterial endotoxin in both structure and biological activity related to physiological function," *Adv. Exp. Med. Biol.*, 256:159-162 (1990).

Kawazoe et al., "Phospholipids and a Novel Glycine-Containing Lipoamino Acid in *Cytophaga johnsonae* Stanier Strain C21," *J. Bacteriol.*, 173(17):5470-5475 (1991).

Kliewer et al., "A Prostaglandin J$_2$ Metabolite Binds Peroxisome Proliferator-Activated Receptor γ and Promotes Adipocyte Differentiation," *Cell*, 83(5):813-819 (1995).

Kliewer et al., "Differential expression and activation of a family of murine peroxisome proliferator-activated receptors," *Proc. Natl. Acad. Sci. USA*, 91(15):7355-7359 (1994).

Kliewer et al., "Fatty acids and eicosanoids regulate gene expression through direct interactions with peroxisome proliferator-activated receptors α and γ," *Proc. Natl. Acad. Sci. USA*, 94(9):4318-4323 (1997).

Kohno et al., "Identification of N-arachidonylglycine as the endogenous ligand for orphan G-protein-coupled receptor GPR18," *Biochem. Biophys. Res. Commun.*, 347(3):827-832 (2006).

Lehmann et al., "An Antidiabetic Thiazolidinedione Is a High Affinity Ligand for Peroxisome Proliferator-activated Receptor γ (PPARγ)," *J. Biol. Chem.*, 270(22):12953-12956 (1995).

Lehmann et al., "Peroxisome Proliferator-activated Receptors α and γ Are Activated by Indomethacin and Other Non-steroidal Anti-inflammatory Drugs," *J. Biol. Chem.*, 272(6):3406-3410 (1997).

Lerouge et al., "Isolation and structural characterization of a new non-phosphorylated lipoamino acid from *Mycobacterium phlei*," *Chem. Phys. Lipids*, 49(3):161-166 (1988).

Liu et al., "Activation and Binding of Peroxisome Proliferator-Activated Receptor γ by Synthetic Cannabinoid Ajulemic Acid," *Mol. Pharmacol.*, 63(5):983-992 (2003).

Milman et al., "N-arachidonoyl L-serine, an endocannabinoid-like brain constituent with vasodilatory properties," *Proc. Natl. Acad. Sci. U.S.A.*, 103(7):2428-2433 (2006).

Miyazaki et al., "Stimulation and inhibition of polymorphonuclear leukocytes phagocytosis by lipoamino acids isolated from *Serratia marcescens*," *FEMS Immunol. Med. Microbiol.*, 6(4):265-271 (1993).

Mukherjee et al., "Identification, Characterization, and Tissue Distribution of Human Peroxisome Proliferator-activated Receptor (PPAR) Isoforms PPARγ2 *versus* PPARγ1 and Activation with Retinoid X Receptor Agonists and Antagonists," *J. Biol. Chem.*, 272(12):8071-8076 (1997).

Nagy et al., "Oxidized LDL Regulates Macrophage Gene Expression through Ligand Activation of PPARγ," *Cell*, 93(2):229-240 (1998).

Patel et al., "Tumor suppressor and anti-inflammatory actions of PPARγ agonists are mediated via upregulation of PTEN," *Curr. Biol.*, 11(10):764-768 (2001).

Perkins, "The Rel/NF-κB family: friend and foe," *Trends Biochem. Sci.*, 25:434-440 (2000).

Pertwee, "Cannabinoid receptors and pain," *Prog. Neurobiol.*, 63(5):569-611 (2001).

Pertwee, "The ring test: a quantitative method for assessing the 'cataleptic' effect of cannabis in mice" *Br. J. Pharmacol.*, 46(4):753-763 (1972).

Pestonjamasp et al., "Anandamide synthesis is induced by arachidonate mobilizing agonists in cells of the immune system," *Biochim. Biophys. Acta*, 1394:249-260 (1998).

Prusakiewicz et al., "Selective oxygenation of N-arachidonylglycine by cyclooxygenase-2," *Biochem. Biophys. Res. Commun.*, 296:612-617 (2002).

Ricote et al., "The peroxisome proliferator-activated receptor-γ is a negative regulator of macrophage activation," *Nature*, 391(6662):79-82 (1998).

Samuelson et al., "Mapping of the novel G protein-coupled receptor Gpr18 to distal mouse chromosome 14," *Mamm. Genome*, 7(12):920-921 (1996).

Schuligoi et al., "Sequential induction of prostaglandin E and D synthases in inflammation" *Biochem. Biophys. Res. Commun.*, 335(3):684-689 (2005).

Sheskin et al., "Structural Requirements for Binding of Anandamide-Type Compounds to the Brain Cannabinoid Receptor," *J. Med. Chem.*, 40(5):659-667 (1997).

Simonin et al., "PPAR-γ ligands modulate effects of LPS in stimulated rat synovial fibroblasts," *Am. J. Physiol. Cell Physiol.*, 282(1):C125-C133 (2002).

Spiegelman, "PPAR-γ: Adipogenic Regulator and Thiazolidinedione Receptor," *Diabetes*, 47(4):507-514 (1998).

Straus et al., "15-Deoxy-$\Delta^{12,14}$-prostaglandin J$_2$ inhibits multiple steps in the NF-κB signaling pathway," *Proc. Natl. Acad. Sci. USA*, 97(9):4844-4849 (2000).

Uppenberg et al., "Crystal Structure of the Ligand Binding Domain of the Human Nuclear Receptor PPARγ," *J. Biol. Chem.*, 273(47):31108-31112 (1998).

Walker et al., "Pain modulation by release of the endogenous cannabinoid anandamide," *Proc. Natl. Acad. Sci. U.S.A.*, 96(21):12198-12203 (1999).

Wiles et al., "N-Arachidonyl-glycine inhibits the glycine transporter, GLYT2a," *J. Neurochem.*, 99(3):781-786 (2006).

Xu et al., "Structural determinants of ligand binding selectivity between the peroxisome proliferator-activated receptors," *Proc. Natl. Acad. Sci. USA*, 98(24):13919-13924 (2001).

\* cited by examiner

LIST OF FATTY ACIDS (carbon number:double bond number)

| MAMMALIAN FATTY ACIDS | NON-MAMMALIAN FATTY ACIDS |
|---|---|
| Myristic acid, 14:0 | Pentadecanoic acid, 15:0 |
| Palmitic acid, 16:0 | Heptadecanoic acid, 17:0 |
| Stearic acid, 18:0 | Nonadecanoic acid, 19:0 |
| Oleic acid, 18:1 | Heneicosanoic acid, 21:0 |
| Linoleic acid, 18:2 | 9-Trans-tetradecanoic acid, 14:1T |
| Linolenic acid, 18:3 | 10-Trans-pentadecanoic acid, 15:1T |
| Eicosatrienoic acid, 20:3 | 9-Trans-hexadecenoic acid, 16:1T |
| Arachidonic acid, 20:4 | 10-Heptadecenoic acid, 17:1 |
| Eicosapentenoic acid, 20:5 | 10-Trans-heptadecenoic acid, 17:1T |
| Docosatetraenoic acid, 22:4 | 7-Trans-nonadecenoic acid, 19:1T |
| | 10,13-Nonadecadienoic acid, 19:2 |
| | 11-Trans-eicosenoic acid, 20:1T |
| | 12-Heneicosenoic acid, 21:1 |

Fig. 1

LISTS OF AMINO ACIDS

| NATURAL (L-)AMINO ACIDS | D-AMINO ACIDS |
|---|---|
| Glycine | D-Glycine |
| Alanine | D-Alanine |
| Valine | D-Valine |
| Leucine | D-Leucine |
| Isoleucine | D-Isoleucine |
| Serine | D-Serine |
| Threonine | D-Threonine |
| Methionine | D-Methionine |
| Phenylalanine | D-Phenylalanine |
| Tyrosine | D-Tyrosine |
| Proline | D-Proline |
| Lysine | D-Lysine |
| Aspartic acid | D-Aspartic acid |
| Glutamic acid | D-Glutamic acid |
| Asparagine | D-Asparagine |
| Glutamine | D-Glutamine |

Fig. 2

AMINO ACID ANALOGS (i) 1-amino-cyclohexane carboxylic acid (ii) 1-amino-cyclopentane carboxylic acid (iii) 1-amino-cyclopropane carboxylic acid (iv) 2-aminoisobutyric acid $R=NH_2$ (i)     (ii)     (iii)     (iv)

*PHENYL GLYCINE & DERIVATIVES*

| NAME | X |
|---|---|
| Phenyl Glycine | H |
| | OH |
| | $CH_2NH_2$ |
| | $SO_3$ |

PHENYL ALANINE DERIVATIVES

| X | Y | Z |
|---|---|---|
| H | OH | H |
| H | OCH$_3$ | H |
| H | H | OH |
| H | H | OCH$_3$ |
| I | H | H |
| CH$_3$ | H | H |
| NH-CO-CH$_3$ | H | H |
| SH | H | H |
| NH$_2$ | H | H |
| Cl | H | H |
| CN | H | H |
| CH$_2$NH$_2$ | H | H |
| COOH | H | H |
| NO$_2$ | H | H |
| CHO | H | H |
| C$_2$H$_5$ | H | H |
| i-C$_3$H$_7$ | H | H |
| OCH$_3$ | H | H |
| CONH$_2$ | H | H |
| COCH$_3$ | H | H |
| H | NO$_2$ | H |
| F | H | H |
| H | NH$_2$ | H |
| CH$_2$OH | H | H |

EXEMPLARY DIPEPTIDES

Glycine-2-aminoisobutyric acid

Alanine-2-aminoisobutyric acid

Glycine-1-amino-cyclopentane carboxylic acid

Alanine-1-amino-cyclopentane carboxylic acid

Glycine-glycine-COOH  (available from Sigma-Aldrich)

Glycine-alanine-COOH  (available from Sigma-Aldrich)

Alanine-glycine-COOH  (available from Sigma-Aldrich)

Alanine-alanine-COOH  (available from Sigma-Aldrich)

Fig. 6

General Synthesis Scheme for Protocol #1 and Protocol #2

General Synthesis Scheme for Protocol #3

$J_2$ Prostanoids
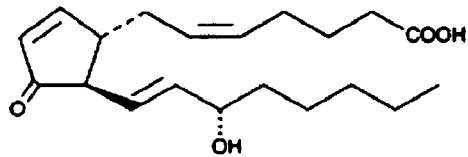
Prostaglandin $J_2$
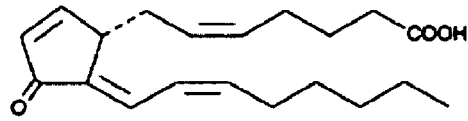
15-deoxy-$\Delta^{12,14}$-prostaglandin $J_2$
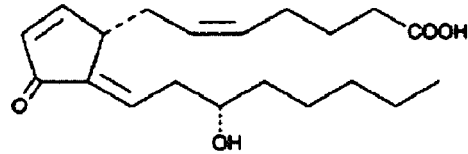
$\Delta^{12}$-prostaglandin $J_2$
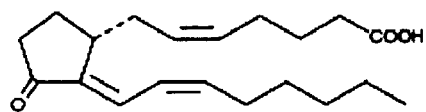
9,10-dihydro-15-deoxy-$\Delta^{12,14}$-prostaglandin $J_2$ (CAY10410)
Fig. 9

LIPID-AMINO ACID CONJUGATES AND METHODS OF USE

CROSS-REFERENCE TO RELATED APPLICATIONS

This application claims the benefit of the filing date of U.S. Provisional Patent Application Ser. No. 60/588,697, filed on Jul. 16, 2004. The contents of this prior application are hereby incorporated by reference in their entirety.

STATEMENT AS TO FEDERALLY SPONSORED RESEARCH

This invention was made with support from NIH grant numbers DA12178 and DA017969; therefore, the government has certain rights in the invention.

TECHNICAL FIELD

This invention relates to lipid-amino acid conjugates and methods of making and using the conjugates in the treatment of conditions that involve, for example, dysfunctional lipid metabolism, insulin sensitivity, glucose homeostasis, and/or inflammation. The invention relates to the fields of molecular biology, medicinal chemistry, pharmacology, and medicine.

BACKGROUND

Lipoamino acids are a class of molecules first identified in bacteria that consist of a fatty acid moiety conjugated to an amino acid (Kawazoe et al., *J. Bacteriol.*, 173:5470-5475, 1991). At least three fatty acid-amino acid conjugates are natural constituents of the mammalian brain: N-arachidonylglycine (NAGly), N-arachidonyl-4-aminobutyric acid (NAGABA), and N-arachidonylalanine (NAAla). NAGly is an endogenous constituent of many tissues, including spinal cord, small intestines, kidneys, glabourous skin, heart, lung, liver, spleen, testes, and blood (Huang et al., *J. Biol. Chem.*, 276:46, 2001). NAGly is a structural analog of the endogenous cannabinoid anandamide, although it has been reported to lack affinity for the cannabinoid receptors CB1 and CB2, the vanilloid VR1 receptor, and the anandamide transporter (Huang et al., 2001, supra; Burstein et al., *Prostaglandins and Other Lipid Mediat.*, 61:29-41, 2000). NAGly has been reported to have analgesic properties.

SUMMARY

The present invention relates to lipid-amino acid conjugates, for example, N-fatty acid-amino acid conjugates, which can be referred to as "elmiric acids," and $J_2$ prostanoid-amino acid conjugates, which can be referred to as "J acids," methods of synthesizing such conjugates, and methods of treating various disorders, including, e.g., inflammation, pain, conditions related to dysfunctional lipid metabolism, HIV, and type II diabetes, with such conjugates.

Certain conjugates disclosed herein have the following general formula (Formula I):

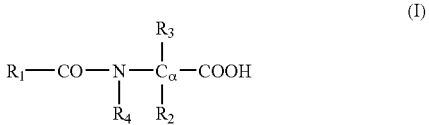

In Formula I, $R_1$, $R_2$, $R_3$, and $R_4$ represent chemical groups. The conjugates disclosed have at least one of the following features: (a) $R_1$ is a substituent of a non-mammalian fatty acid or (b) $R_2$ and $R_3$ are substituents of an amino acid analog. $R_1$ can be the non-carboxyl portion (tail) of a $J_2$ prostanoid, e.g., a mammalian or a non-mammalian $J_2$ prostanoid, or a fatty acid, e.g., a mammalian fatty acid or a non-mammalian fatty acid. Certain compounds disclosed herein have the structure of Formula I, in which $R_1$ is the hydrocarbon chain of a mammalian fatty acid, and $R_2$, $R_3$, and $R_4$ are substituents of an amino acid analog. Other compounds disclosed herein have the structure of Formula I, in which $R_1$ is a tail (non-carboxyl portion) of a non-mammalian fatty acid or $J_2$ prostanoid, and $R_2$, $R_3$, and $R_4$ are substituents of (i) a natural amino acid or (ii) an amino acid analog.

Other conjugates disclosed herein include a dipeptide conjugated to a fatty acid or $J_2$ prostanoid.. These conjugates have the following general formula (Formula II):

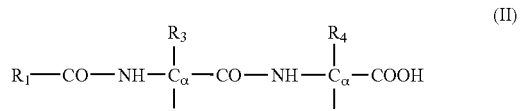

In Formula II, $R_1$ can be the hydrocarbon chain of either a $J_2$ prostanoid or a mammalian or non-mammalian fatty acid. The pairs of substituents $R_2$ and $R_3$, and $R_4$ and $R_5$, each form an amino acid residue in combination with the respective alpha carbon. In Formula II, each amino acid can be, independently, a natural amino acid or an amino acid analog.

Thus, in one aspect, a conjugate disclosed herein has the structure of Formula I, and $R_1$ is the hydrocarbon chain of a mammalian fatty acid, e.g., myristic acid, palmitic acid, stearic acid, oleic acid, linoleic acid, linolenic acid, eicosatrienoic acid, arachidonic acid, eicosapentenoic acid, and docosatetraenoic acid. In some embodiments of this aspect, $R_4$ is a hydrogen, and $R_2$ and $R_3$ together form a cyclic side chain of an amino acid analog, such as 1-amino-cyclopropane carboxylic acid, 1-amino-cyclopentane carboxylic acid, and 1-amino-cyclohexane carboxylic acid. In other embodiments, $R_4$ is, e.g., a hydrogen, and $R_2$ and $R_3$ are the two methyl groups of 2-aminoisobutyric acid. In still other embodiments, $R_3$ and $R_4$ are, e.g., hydrogens, and $R_2$ is the side chain of a phenyl-glycine or a phenyl-glycine derivative. In yet other embodiments, $R_3$ and $R_4$ are, e.g., hydrogens, and $R_2$ is the side chain of a phenyl-alanine derivative. In other embodiments, $R_3$ is, e.g., a hydrogen, and $R_2$ and $R_4$ together form the side chain of a proline derivative. In different embodiments, $R_3$ and $R_4$ are, e.g., hydrogens, and $R_2$ is the side chain of an amino acid selected from the group consisting of: serine, threonine, methionine, phenylalanine, tyrosine, lysine, aspartic acid, and glutamic acid, and the Cα has the same stereochemistry as a D amino acid. In further embodiments, $R_3$ is, e.g., a hydrogen, and $R_2$ and $R_4$, together, form D-proline. In certain embodiments, $R_4$ can be a hydrogen, methyl or ethyl group.

In another aspect, a conjugate disclosed herein has the structure of Formula I, and $R_1$ is the hydrocarbon chain of arachidonic acid. In some embodiments of this aspect, $R_4$ is, e.g., a hydrogen, and $R_2$ and $R_3$ together form the cyclic side chain of an amino acid analog, such as, 1-amino-cyclopropane carboxylic acid, 1-amino-cyclopentane carboxylic acid, and 1-amino-cyclohexane carboxylic acid. In other embodiments, $R_4$ is, e.g., a hydrogen, and $R_2$ and $R_3$ are the two methyl groups of 2-aminoisobutyric acid. In still other embodiments, $R_3$ and $R_4$ are, e.g., hydrogens, and $R_2$ is the side chain of a phenyl-glycine or a phenyl-glycine derivative. In yet other embodiments, $R_3$ and $R_4$ are, e.g., hydrogens, and $R_2$ is the side chain of a phenyl-alanine derivative. In other embodiments, $R_3$ is, e.g., a hydrogen, and $R_2$ and $R_4$ together form the side chain of a proline derivative. In different embodiments, $R_3$ and $R_4$ are, e.g., hydrogens, and $R_2$ is the side chain of an amino acid selected from the group consisting of: serine, threonine, methionine, phenylalanine, tyrosine, lysine, aspartic acid, and glutamic acid, and the Cα has the same stereochemistry as a D amino acid. In further embodiments, $R_3$ is, e.g., a hydrogen, and $R_2$ and $R_4$, together, form D-proline. In certain embodiments, $R_4$ can be a hydrogen, methyl or ethyl group.

In a different aspect, a conjugate disclosed herein has the structure of Formula I, and $R_1$ is the hydrocarbon chain of a non-mammalian fatty acid, e.g., pentadecanoic acid; heptadecanoic acid; nonadecanoic acid; heneicosanoic acid; 9-trans-tetradecanoic acid, 14:1 T; 10-trans-pentadecanoic acid, 15:1 T; 9-trans-hexadecenoic acid, 16:1 T; 10-heptadecenoic acid, 17:1; 10-trans-heptadecenoic acid, 17:1 T; 7-trans-nonadecenoic acid, 19:1T; 10,13-nonadecadienoic acid, 19:2; 11-trans-eicosenoic acid, 20:1T; and 12-heneicosenoic acid, 21:1. In some embodiments of this aspect, $R_4$ is, e.g., a hydrogen, and $R_2$ and $R_3$ together form the cyclic side chain of an amino acid analog, e.g., 1-amino-cyclopropane carboxylic acid, 1-amino-cyclopentane carboxylic acid, and 1-amino-cyclohexane carboxylic acid. In other embodiments, 4 is, e.g., a hydrogen, and $R_2$ and $R_3$ are the two methyl groups of 2-aminoisobutyric acid. In still other embodiments, $R_3$ and $R_4$ are, e.g., hydrogens, and $R_2$ is the side chain of a phenyl-glycine or a phenyl-glycine derivative. In yet other embodiments, $R_3$ and $R_4$ are, e.g., hydrogens, and $R_2$ is the side chain of a phenyl-alanine derivative. In other embodiments, $R_3$ is, e.g., a hydrogen, and $R_2$ and $R_4$ together form the side chain of a proline or a proline derivative. In certain other embodiments, $R_3$ and $R_4$ are, e.g., hydrogens, and $R_2$ is the side chain of a D- or L-enantiomer of an amino acid, e.g., glycine, alanine, valine, leucine, isoleucine, serine, threonine, methionine, phenylalanine, tyrosine, lysine, aspartic acid, glutamic acid, asparagine, and glutamine. In certain embodiments, $R_4$ can be a hydrogen, methyl or ethyl group.

In another aspect, a conjugate disclosed herein has the structure of Formula I, and $R_1$ is the non-carboxyl portion of a $J_2$ prostanoid, e.g., prostaglandin $J_2$, 15-deoxy-$\Delta^{12,14}$-prostaglandin $J_2$, $\Delta^{12}$-prostaglandin $J_2$, or 9,10-dihydro-15-deoxy-$\Delta^{12,14}$-prostaglandin $J_2$. In some embodiments of this aspect, $R_4$ is, e.g., a hydrogen, and $R_2$ and $R_3$ together form the cyclic side chain of an amino acid analog, e.g., 1-aminocyclopropane carboxylic acid, 1-amino-cyclopentane carboxylic acid, and 1-amino-cyclohexane carboxylic acid. In other embodiments, $R_4$ is, e.g., a hydrogen, and $R_2$ and $R_3$ are the two methyl groups of 2-aminoisobutyric acid. In still other embodiments, $R_3$ and $R_4$ are, e.g., hydrogens, and $R_2$ is the side chain of a phenyl-glycine or a phenyl-glycine derivative. In yet other embodiments, $R_3$ and $R_4$ are, e.g., hydrogens, and $R_2$ is the side chain of a phenyl-alanine derivative.

In other embodiments, $R_3$ is, e.g., a hydrogen, and $R_2$ and $R_4$ together form the side chain of a proline or a proline derivative. In certain other embodiments, $R_3$ and $R_4$ are, e.g., hydrogens, and $R_2$ is the side chain of a D- or L-enantiomer of an amino acid, e.g., glycine, alanine, valine, leucine, isoleucine, serine, threonine, methionine, phenylalanine, tyrosine, lysine, aspartic acid, glutamic acid, asparagine, and glutamine. In certain embodiments, $R_4$ can be a hydrogen, methyl or ethyl group.

In yet another aspect, a conjugate disclosed herein has the structure of Formula II, and $R_1$ can be the hydrocarbon chain of a $J_2$ prostanoid or a fatty acid, e.g., a mammalian fatty acid or a non-mammalian fatty acid. In this aspect, $R_2$ and $R_3$ are substituents of a natural amino acid or an amino acid analog; and $R_4$ and $R_5$ are substituents of a natural amino acid or an amino acid analog, such that the compound consists of a fatty acid amide linked to a dipeptide.

In another aspect, the invention provides pharmaceutical compositions that include one or more of the conjugates disclosed herein. These pharmaceutical compositions can be used in the methods of treatment that constitute yet another aspect of the invention. In these methods of treatment, a pharmaceutical composition that includes a therapeutically effective amount of one or more conjugates described herein is administered to a subject suffering from a medical condition, such as inflammation, e.g., psoriasis or rheumatoid arthritis, type 2 diabetes, and/or the side effects associated with antiviral protease inhibitors, such as anti-HIV protease cocktails, to treat such condition.

A "lipid-amino acid conjugate" is an N-conjugate of a lipid acid, e.g., a $J_2$ prostanoid or fatty acid, and an amino acid.

"Elmiric acid," as used herein, refers to an N-fatty acid-amino acid conjugate with a structure described by Formula I or Formula II, as defined herein.

"J acid," as used herein, refers to a $J_2$ prostanoid-amino acid conjugate wikth a structure described by Formula I or Formula II, as defined herein.

"N-fatty acid-amino acid conjugate" is used herein interchangeably with "N-fatty acid-amino conjugate."

A mammalian fatty acid is a natural or synthetic fatty acid that is identical in structure to one naturally produced in a mammal, including, but not limited to, myristic acid, palmitic acid, stearic acid, oleic acid, linoleic acid, linolenic acid, eicosatrienoic acid, arachidonic acid, eicosapentenoic acid, and docosatetraenoic acid.

A non-mammalian fatty acid is a natural or synthetic fatty acid not normally produced by a mammal, including, but not limited to, pentadecanoic acid; heptadecanoic acid; nonadecanoic acid; heneicosanoic acid; 9-trans-tetradecanoic acid, 14:1T; 10-trans-pentadecanoic acid, 15:1T; 9-trans-hexadecenoic acid, 16:1T; 10-heptadecenoic acid, 17:1; 10-trans-heptadecenoic acid, 17:1T; 7-trans-nonadecenoic acid, 19:1T; 10,13-nonadecadienoic acid, 19:2; 11-trans-eicosenoic acid, 20:1T; and 12-heneicosenoic acid, 21:1.

$J_2$ prostanoid, as used herein, refers to prostaglandin J2 and its derivatives and analogs, including but not limited to 15-deoxy-$\Delta^{12,14}$-prostaglandin $J_2$, $\Delta^{12}$-prostaglandin $J_2$, and 9,10-dihydro-15-deoxy-$\Delta^{12,14}$-prostaglandin $J_2$.

The term "natural amino acid," as used herein, refers to L-amino acids found in nature and excludes D-amino acids and amino acid analogs.

The term "amino acid analog," as used herein, includes non-naturally occurring L-amino acids and D-amino acids, whether naturally or non-naturally occurring, as well as N-substituted amino acids, e.g., N-methyl and N-ethyl amino acids.

Dipeptides, as used herein, refers to two amide linked chemical groups, wherein each chemical group is independently a natural amino acid or an amino acid analog.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF DRAWINGS

FIG. 1 is a list of exemplary fatty acids that can be used to make an elmiric acid.

FIG. 2 is a list of exemplary amino acids that can be used to make an elmiric acid or J acid.

FIG. 6 is a list of exemplary dipeptides that can be used to make an elmiric acid or J acid.

FIG. 9 is a list of exemplary $J_2$ prostanoids that can be used to make a J acid.

DETAILED DESCRIPTION

Lipid-amino acid conjugates, e.g., elmiric acids (N-fatty acid-amino acid conjugates) and J acids ($J_2$ prostanoid-amino acid conjugates), and methods of making and using them are disclosed herein. These conjugates contain at least one of the following chemical groups: a non-mammalian fatty acid, a $J_2$ prostanoid, an amino acid analog, or a dipeptide. To facilitate appreciation of the invention, the conjugates can be classified in three groups. In a first group, the conjugates contain the hydrocarbon chain (tail) of a mammalian fatty acid, the carboxyl group of which has reacted with the amino residue of an amino acid analog to form an amide linked N-fatty acid-amino acid conjugate. In a second group, the conjugates contain the non-carboxyl portion (tail) of a non-mammalian fatty acid or a $J_2$ prostanoid, the carboxyl group of either of which has reacted with the amino residue of either an amino acid analog or a natural amino acid to form an amide linked N-fatty acid-amino acid conjugate or an amide linked $J_2$ prostanoid-amino acid conjugate. In a third group, the conjugates contain a dipeptide, the amino terminus of which has reacted with the carboxyl group of either a $J_2$ prostanoid, a mammalian fatty acid, or a non-mammalian fatty acid to form an amide linked N-fatty acid-amino acid conjugate or an amide linked $J_2$ prostanoid-amino acid conjugate. The phrase "has reacted with," as used above, simply provides help in the visualization of the structure, and is not an implicit limitation on how the compounds can be made. These elmiric acids and J acids can be used to treat various disorders, including those associated with dysfunctional lipid metabolism, insulin sensitivity, glucose homeostasis, and/or inflammation.

Lipid-Amino Acid Conjugates

Certain lipid-amino acid conjugates disclosed can be represented by the following general formula (Formula I):

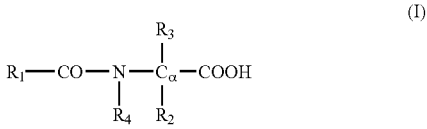

(I)

In Formula I, $C_\alpha$ is the alpha-carbon of a natural amino acid or an amino acid analog. The $R_1$, $R_2$, $R_3$, and $R_4$ groups are as defined elsewhere herein.

1. Elmiric Acids Including a Mammalian Fatty Acid

In one aspect, an elmiric acid has the structure of Formula I, and $R_1$ is the hydrocarbon chain (or tail) of a mammalian fatty acid, e.g., myristic acid, 14:0; palmitic acid, 16:0; stearic acid, 18:0; oleic acid, 18:1; linoleic acid, 18:2; linolenic acid, 18:3; eicosatrienoic acid, 20:3; arachidonic acid, 20:4; eicosapentenoic acid, 20:5; or docosatetraenoic acid, 22:4. Exemplary mammalian fatty acids are listed in FIG. 1. All of the compounds listed in FIG. 1 are available from Nu-Check Prep, Inc. (Elysian, Minn.).

Figure 3:
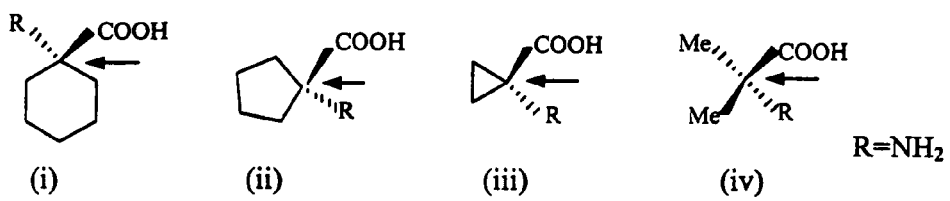
FIG. 3 is a list of exemplary cyclic amino acid analogs that can be used to make an elmiric acid or J acid. The arrow denotes the alpha carbon of the amino acid analog, and R denotes the amino group, which can be used to form an amide linkage to a fatty acid molecule or $J_2$ prostanoid, thereby forming an N-fatty acid-amino acid conjugate or $J_2$ prostanoid-amino acid conjugate.

In certain embodiments of this aspect, $R_4$ is, e.g., a hydrogen, and $R_2$ and $R_3$ together form the cyclic side chain of an amino acid analog that can be, e.g., 1-amino-cyclopropane carboxylic acid, 1-amino-cyclopentane carboxylic acid, or 1-amino-cyclohexane carboxylic acid. In other embodiments, 4 is, e.g., a hydrogen, and $R_2$ and $R_3$ represent the two methyl side chains of 2-aminoisobutyric acid. In both of these embodiments where $R_2$ and $R_3$ are substituents of an amino acid analog depicted in FIG. 3, the alpha-carbon of Formula I is the carbon marked by an arrow in FIG. 3. The "R" in FIG. 3 denotes the amino group that can be used to form an amide linkage to a fatty acid molecule, thereby forming an N-fatty acid-amino acid conjugate. All of the amino acid analogs listed in FIG. 3 are available from Sigma-Aldrich (St. Louis, Mo.).

In other embodiments, $R_2$ is the phenyl side chain of a phenylglycine or a phenyl-glycine derivative, such that $R_2$ has the following general structure (Formula III):

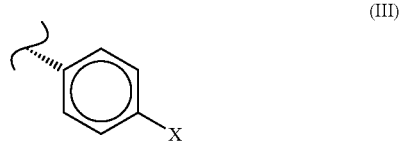

(III)

Figure 4:
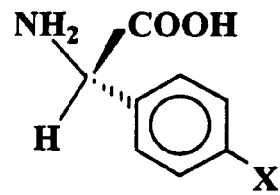
FIG. 4 is a list of exemplary amino acid analogs, including phenyl-glycine and phenyl-glycine derivatives, that can be used to make an elmiric acid or J acid.

In these embodiments, $R_3$ and $R_4$ are, e.g., H, and $R_2$ has the structure of Formula III, wherein X can be, e.g., H, OH, $CH_2NH_2$, and $SO_3$. Exemplary phenyl-glycine derivatives are listed in FIG. 4, all of which are available from RSP Amino Acid Analogues, Inc. (Hopkinton, Mass.).

In yet other embodiments, $R_2$ is a methylene-phenyl side chain of a phenylalanine derivative, such that $R_2$ has the following general structure (Formula IV):

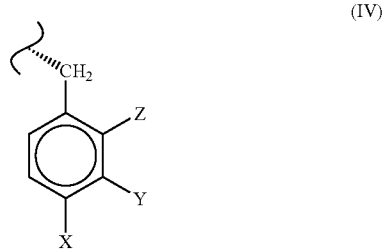

(IV)

Figure 5:
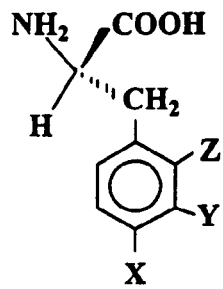
FIG. 5 is a list of exemplary phenyl-alanine derivatives that can be used to make an elmiric acid or J acid.

In these embodiments, $R_3$ and $R_4$ are, e.g., H, and $R_2$ has the structure of Formula IV, wherein the set of substituents corresponding to X, Y, and Z, can independently be, e.g., H, OH, $OCH_3$, F, Cl, I, $CH_3$, $C_2H_5$, $i$-$C_3H_7$, $NH$—$CO$—$CH_3$, SH, $NH_2$, CN, $CH_2NH_2$, COOH, CHO, $NO_2$, $CONH_2$, $COCH_3$, or $CH_2OH$. In specific examples, X, Y, and Z (X, Y, Z), respectively, can be: (H, OH, H); (H, $OCH_3$, H); (H, H, OH); (H, H, $OCH_3$); (I, H, H); ($CH_3$, H, H); ($NH$—$CO$—$CH_3$, H, H); (SH, H, H); ($NH_2$, H, H); (Cl, H, H); (CN, H, H); ($CH_2NH_2$, H, H); (COOH, H, H); ($NO_2$, H, H); (CHO, H, H); ($C_2H_5$, H, H); ($i$-$C_3H_7$, H, H); ($OCH_3$, H, H); ($CONH_2$, H, H); ($COCH_3$, H, H); (H, $NO_2$, H); (F, H, H); (H, $NH_2$, H), and ($CH_2OH$, H, H). Note that in the immediately preceding group of substituent sets, each set of substituents marked off by parenthesis is arranged in the following manner (X substituent, Y substituent, and Z substituent), consistent with the phenylalanine derivatives shown in FIG. 5. All of the compounds listed in FIG. 5 are available from RSP Amino Acid Analogues, Inc.

In still other embodiments, $R_3$ is, e.g., H and $R_2$ and $R_4$ together form a proline derivative, such that $R_2$ and $R_4$ together form one of the following structures (Formulas V, VI, and VII):

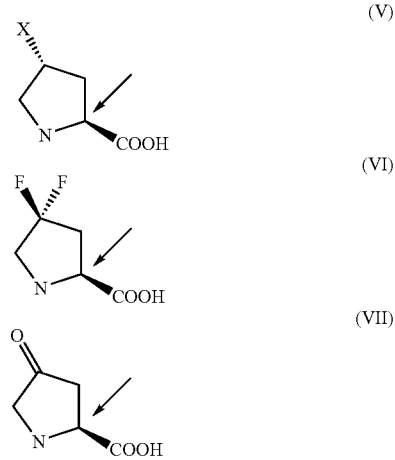

In these embodiments, $R_2$ and $R_4$ together form the structure of any one of Formulas V, VI, and VII and the arrow denotes the α-carbon of Formula I. The $R_1$ hydrocarbon chain of a fatty acid is amide linked to the nitrogen molecule in the ring structure of Formulas V, VI, and VII, thereby forming an N-fatty acid-amino acid conjugate. In embodiments where $R_2$ and $R_4$ form the ring structure of Formula V, X can be, e.g., CN, CHO, $CH_2OH$, $CH_2NH_2$, COOH, $CH_2CN$, $NH_2$, or phenyl.

In further embodiments, $R_3$ and $R_4$ are, e.g., hydrogens, and $R_2$ forms a D-amino acid (other than glycine) listed in FIG. 2. $R_2$ can be the side chain of a D-amino acid such as alanine, valine, leucine, isoleucine, serine, threonine, methionine, phenylalanine, tyrosine, lysine, aspartic acid, glutamic acid, asparagine, or glutamine. In other embodiments of this aspect, $R_2$ and $R_3$ are, e.g., H, thereby forming a glycine conjugate. In other embodiments, $R_3$ is H, and $R_2$ and $R_4$ together form D-proline. The amino acids listed in FIG. 2 are available from Sigma-Aldrich.

2. Elmiric Acids Including Non-Mammalian Fatty Acids

In another aspect, an elmiric acid has the structure of Formula I, and $R_1$ is the hydrocarbon chain (tail) of a non-mammalian fatty acid, such as pentadecanoic acid, 15:0; heptadecanoic acid, 17:0; nonadecanoic acid, 19:0; heneicosanoic acid, 21:0; 9-trans-tetradecanoic acid, 14:1 T; 10-trans-pentadecanoic acid, 15:1 T; 9-trans-hexadecenoic acid, 16:1 T; 10-heptadecenoic acid, 17:1; 10-trans-heptadecenoic acid, 17:1T; 7-trans-nonadecenoic acid, 19:1T; 10,13-nonadecadienoic acid, 19:2; 11-trans-eicosenoic acid, or 20:1 T; 12-heneicosenoic acid, 21:1. Exemplary non-mammalian fatty acids are listed in FIG. 1.

In some embodiments of this aspect, $R_3$ and $R_4$ are, e.g., H and $R_2$ is the side chain of a D- or L-isomer of an amino acid such as alanine, valine, leucine, isoleucine, serine, threonine, methionine, phenylalanine, tyrosine, lysine, aspartic acid, glutamic acid, asparagine, or glutamine. In other embodiments of this aspect, $R_2$, $R_3$, and $R_4$ are H, thereby forming a glycine conjugate.

In other embodiments, $R_4$ is, e.g., H, and $R_2$ and $R_3$ together form the cyclic side chain of an amino acid analog that can be 1-amino-cyclopropane carboxylic acid, 1-amino-cyclopentane carboxylic acid, or 1-amino-cyclohexane carboxylic acid. In other embodiments, $R_2$ and $R_3$ represent the two methyl side chains of 2-aminoisobutyric acid. In both of these embodiments where $R_2$ and $R_3$ are substituents of an amino acid analog depicted in FIG. 3, the alpha-carbon of Formula I is the carbon marked by an arrow in FIG. 3. The "R" in FIG. 3 denotes the amino group that can be used to form an amide linkage to a fatty acid molecule, thereby forming an N-fatty acid-amino acid conjugate.

In still other embodiments, $R_3$ and $R_4$ are, e.g., H, and $R_2$ is the side chain of a phenyl-glycine or a phenyl-glycine derivative, such that $R_2$ has the general structure of Formula III, and X can be, e.g., H, OH, $CH_2NH_2$, or $SO_3$.

In yet other embodiments, $R_3$ and $R_4$ are, e.g., H, and $R_2$ is the side chain of a phenylalanine derivative, such that $R_2$ has the general structure of Formula IV, wherein the set of substituents corresponding to X, Y, and Z, can independently be, e.g., H, OH, $OCH_3$, F, Cl, I, $CH_3$, $C_2H_5$, $i$-$C_3H_7$, $NH$—$CO$—$CH_3$, SH, $NH_2$, CN, $CH_2NH_2$, COOH, CHO, $NO_2$, $CONH_2$, $COCH_3$, or $CH_2OH$. In specific examples, X, Y, and Z (X, Y, Z), respectively, can be: (H, OH, H); (H, $OCH_3$, H); (H, H, OH); (H, H, $OCH_3$); (I, H, H); ($CH_3$, H, H); ($NH$—$CO$—$CH_3$, H, H); (SH, H, H); ($NH_2$, H, H); (Cl, H, H); (CN, H, H); ($CH_2NH_2$, H, H); (COOH, H, H); ($NO_2$, H, H); (CHO, H, H); ($C_2H_5$, H, H); ($i$-$C_3H_7$, H, H); ($OCH_3$, H, H); ($CONH_2$, H, H); ($COCH_3$, H, H); (H, $NO_2$, H); (F, H, H); (H, $NH_2$, H), and ($CH_2OH$, H, H). Note that in the immediately preceding group of substituent sets, each set of substituents marked off by parenthesis is arranged in the following manner (X substituent, Y substituent, and Z substituent), consistent with the phenylalanine derivatives shown in FIG. 5.

In certain other embodiments, $R_3$ is, e.g., H, and $R_2$ and $R_4$ together form a proline or the structure of any one of Formulas V, VI, and VII and the arrow denotes the α-carbon of Formula I. The $R_1$ hydrocarbon chain of a fatty acid is amide linked to the nitrogen molecule in the ring structure of Formulas V, VI, and VII, thereby forming an N-fatty acid-amino acid conjugate. In embodiments where $R_2$ and $R_4$ form the ring structure of Formula V, X can be, e.g., CN, CHO, $CH_2OH$, $CH_2NH_2$, COOH, $CH_2CN$, $NH_2$, or phenyl.

3. N-Fatty Acid-Dipeptide Amino Acid Conjugates

In another aspect, an elmiric acid includes a dipeptide conjugated to a fatty acid. These conjugates have the following general formula (formula II):

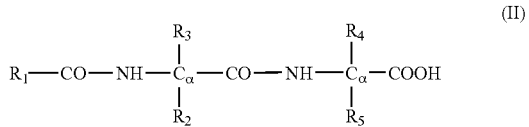

($R_2$ and $R_3$) and ($R_4$ and $R_5$) are substituents of two amino acids that include the depicted alpha carbons, thereby creating a dipeptide that is amide linked to a fatty acid. The dipeptide can consist of two natural amino acids, two amino acid analogs, or one natural amino acid and one amino acid analog. In some embodiments, ($R_2$ and $R_3$) and/or ($R_4$ and $R_5$) are substituents of a D-amino acid, an L-amino acid, or an amino acid analog. In some embodiments, $R_2$ and $R_3$ together form the cyclic side chain of an amino acid analog with a cyclic side chain. In some embodiments, $R_4$ and $R_5$ together form the cyclic side chain of an amino acid analog with a cyclic side chain. In some embodiments, $R_2$ and $R_3$ are the two methyl groups of aminoisobutyric acid. In some embodiments, $R_4$ and $R_5$ are the two methyl groups of aminoisobutyric acid. Exemplary N-fatty acid-dipeptide amino acid conjugates include dipeptides such as glycine-2-aminoisobutyric acid, alanine-2-aminoisobutyric acid, glycine-1-amino-cyclopentane carboxylic acid, alanine-1-amino-cyclopentane carboxylic acid, glycine-glycine-COOH, glycine-alanine-COOH, alanine-glycine-COOH, and alanine-alanine-COOH.

In some embodiments of this conjugate, $R_1$ can be the hydrocarbon chain (tail) of a mammalian fatty acid such as myristic acid 14:0; palmitic acid, 16:0; stearic acid, 18:0; oleic acid, 18:1; linoleic acid, 18:2; linolenic acid, 18:3; eicosatrienoic acid, 20:3; arachidonic acid, 20:4; eicosapentenoic acid, 20:5; docosatetraenoic acid, 22:4.

In other embodiments, $R_1$ can be the hydrocarbon chain (tail) of an non-mammalian fatty such as pentadecanoic acid, 15:0; heptadecanoic acid, 17:0; nonadecanoic acid, 19:0; heneicosanoic acid, 21:0; 9-trans-tetradecanoic acid, 14:1T; 10-trans-pentadecanoic acid, 15:1 T; 9-trans-hexadecenoic acid, 16:1 T; 10-heptadecenoic acid, 17:1; 10-trans-heptadecenoic acid, 17:1T; 7-trans-nonadecenoic acid, 19:1T; 10,13-nonadecadienoic acid, 19:2; 11-trans-eicosenoic acid, 20:1T; and 12-heneicosenoic acid, 21:1.

4. $J_2$ Prostanoid-Amino Acid Conjugates

In another aspect, a J acid has the structure of Formula I, and $R_1$ is the non-carboxyl portion (tail) of a $J_2$ prostanoid, e.g., prostaglandin $J_2$, 15-deoxy-$\Delta^{12,14}$-prostaglandin $J_2$, $\Delta^{12}$-prostaglandin $J_2$, or 9,10-dihydro-15-deoxy-$\Delta^{12,14}$-prostaglandin $J_2$ (CAY10410). Exemplary J2 prostanoids are depicted in FIG. 9, all of which are available from Cayman Chemical Company (Ann Arbor, Mich.).

In some embodiments of this aspect, $R_3$ and $R_4$ are, e.g., H and $R_2$ is the side chain of a D- or L-isomer of an amino acid such as alanine, valine, leucine, isoleucine, serine, threonine, methionine, phenylalanine, tyrosine, lysine, aspartic acid, glutamic acid, asparagine, or glutamine. In other embodiments of this aspect, $R_2$, $R_3$, and $R_4$ are H, thereby forming a glycine conjugate.

In other embodiments, $R_4$ is, e.g., H, and $R_2$ and $R_3$ together form the cyclic side chain of an amino acid analog that can be 1-amino-cyclopropane carboxylic acid, 1-amino-cyclopentane carboxylic acid, or 1-amino-cyclohexane carboxylic acid. In other embodiments, $R_2$ and $R_3$ represent the two methyl side chains of 2-aminoisobutyric acid. In both of these embodiments where $R_2$ and $R_3$ are substituents of an amino acid analog depicted in FIG. 3, the alpha-carbon of Formula I is the carbon marked by an arrow in FIG. 3. The "R" in FIG. 3 denotes the amino group that can be used to form an amide linkage to a fatty acid molecule, thereby forming an N-fatty acid-amino acid conjugate.

In still other embodiments, $R_3$ and $R_4$ are, e.g., H, and $R_2$ is the side chain of a phenyl-glycine or a phenyl-glycine derivative, such that $R_2$ has the general structure of Formula III, and X can be, e.g., H, OH, $CH_2NH_2$, or $SO_3$.

In yet other embodiments, $R_3$ and $R_4$ are, e.g., H, and $R_2$ is the side chain of a phenylalanine derivative, such that $R_2$ has the general structure of Formula IV, wherein the set of substituents corresponding to X, Y, and Z, can independently be, e.g., H, OH, $OCH_3$, F, Cl, I, $CH_3$, $C_2H_5$, i-$C_3H_7$, NH—CO—$CH_3$, SH, $NH_2$, CN, $CH_2NH_2$, COOH, CHO, $NO_2$, $CONH_2$, $COCH_3$, or $CH_2OH$. In specific examples, X, Y, and Z (X, Y, Z), respectively, can be: (H, OH, H); (H, $OCH_3$, H); (H, H, OH); (H, H, $OCH_3$); (I, H, H); ($CH_3$, H, H); (NH—CO—$CH_3$, H, H); (SH, H, H); ($NH_2$, H, H); (Cl, H, H); (CN, H, H); ($CH_2NH_2$, H, H); (COOH, H, H); ($NO_2$, H, H); (CHO, H, H); ($C_2H_5$, H, H); (i-$C_3H_7$, H, H); ($OCH_3$, H, H); ($CONH_2$, H, H); ($COCH_3$, H, H); (H, $NO_2$, H); (F, H, H); (H, $NH_2$, H), and ($CH_2OH$, H, H). Note that in the immediately preceding group of substituent sets, each set of substituents marked off by parenthesis is arranged in the following manner (X substituent, Y substituent, and Z substituent), consistent with the phenylalanine derivatives shown in FIG. 5.

In certain other embodiments, $R_3$ is, e.g., H and $R_2$ and $R_4$ together form the structure of proline or any one of Formulas V, VI, and VII and the arrow denotes the α-carbon of Formula I. The $R_1$ hydrocarbon chain of a fatty acid is amide linked to the nitrogen molecule in the ring structure of Formulas V, VI, and VII, thereby forming an N-fatty acid-amino acid conjugate. In embodiments where $R_2$ and $R_4$ form the ring structure of Formula V, X can be, e.g., CN, CHO, $CH_2OH$, $CH_2NH_2$, COOH, $CH_2CN$, $NH_2$, or phenyl.

5. $J_2$ Prostanoid-Dipeptide Amino Acid Conjugates

In another aspect, an elmiric acid includes a dipeptide conjugated to a $J_2$ prostanoid, e.g., prostaglandin $J_2$, 15-deoxy-$\Delta^{12,14}$-prostaglandin $J_2$, $\Delta^{12}$-prostaglandin $J_2$, or 9,10-dihydro-15-deoxy-$\Delta^{12,14}$-prostaglandin $J_2$ (CAY10410). These conjugates have the following general formula (Formula II):

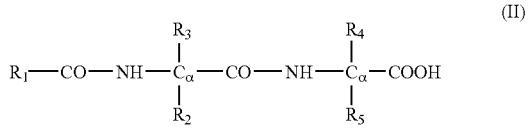

($R_2$ and $R_3$) and ($R_4$ and $R_5$) are substituents of two amino acids that include the depicted alpha carbons, thereby creating a dipeptide that is amide linked to a $J_2$ prostanoid. The dipeptide can consist of two natural amino acids, two amino acid analogs, or one natural amino acid and one amino acid analog. In some embodiments, ($R_2$ and $R_3$) and/or ($R_4$ and $R_5$) are substituents of a D-amino acid, an L-amino acid, or an amino acid analog. In some embodiments, $R_2$ and $R_3$ together form the cyclic side chain of an amino acid analog with a cyclic side chain. In some embodiments, $R_4$ and $R_5$ together form the cyclic side chain of an amino acid analog with a cyclic side chain. In some embodiments, $R_2$ and $R_3$ are the two methyl groups of aminoisobutyric acid. In some embodiments, $R_4$ and $R_5$ are the two methyl groups of aminoisobutyric acid. Exemplary $J_2$ prostanoid-dipeptide amino acid conjugates include dipeptides such as glycine-2-aminoisobutyric acid, alanine-2-aminoisobutyric acid, glycine-1-amino-cyclopentane carboxylic acid, alanine-1-amino-cyclopentane carboxylic acid, glycine-glycine-COOH, glycine-alanine-COOH, alanine-glycine-COOH, and alanine-alanine-COOH.

Methods of Making Lipid-Amino Acid Conjugates

In the protocols that follow, "fatty acid" refers, e.g., to any one of the fatty acids listed in FIG. 1, "$J_2$ prostanoid" refers, e.g., to any one of the compounds depicted in FIG. 9, and amino acid refers, e.g., to any one of the amino acids listed in FIGS. 2-6. As above, $R_1$ refers to the non-carboxyl portion (tail) of a fatty acid or $J_2$ prostanoid, and $R_2$ refers to the side chain of an amino acid. Reaction conditions and concentrations of reagents vary depending on the requirements of the fatty acid or $J_2$ prostanoid and amino acid groups used. Various protocols can be used to prepare non-mammalian fatty acid-amino acid conjugates. The protocols described below can be scaled up or down in volume, and chemically equivalent reagents may be substituted for the reagents indicated.

Amino acid methyl esters can be purchased from commercial vendors, e.g., RSP, Amino Acid Analogues, Inc. Alternatively, amino acid methyl esters can be synthesized by dissolving an amino acid or an amino acid analog (~200 mg to ~2 g) in methanol saturated with HCl (~30 to ~300 ml) and refluxed for 6-12 hours. The solvent is then removed under vacuum and the crude product dissolved in ethyl acetate and partitioned with saturated bicarbonate to remove traces of unreacted amino acid.

Protocol #1

The following protocol describes one method to prepare a lipid-amino acid conjugate, e.g., an elmiric acid or J acid. See FIG. 7 for a general scheme of the protocol. For example, the protocol is suitable for the production of any of the following: D-alanine, D-valine, D-leucine, D-isoleucine, D-phenylalanine, D-asparagine, D-glutamine, and γ-aminobutyric acid conjugates of long-chain fatty acids. These long-chain fatty acids include arachidonic, myristic, palmitic, stearic, oleic, linoleic, eicosatrienoic, eicosapentenoic, and docosatetraenoic acids. The protocol is also suitable for use with any fatty acid, $J_2$ prostanoid, or amino acid group.

Generally the protocol involves the following steps. Prepare a solution of 10 milliequivalents (mequivalents) of amino acid methyl ester HCl in 5-10 ml methylene chloride containing 0.5-1.5 ml of triethylamine and cooling to 0° C. A solution of 10 mequivalents of fatty acid chloride or $J_2$ prostanoid chloride in 2-5 ml methylene chloride is added to the amino acid ester solution and allowed to react for a time sufficient to complete the conjugation, e.g., for 60, 120, 180, or 240 minutes, at 0-4° C. An equal volume of water is added to terminate the reaction, and the reaction is then extracted with ethyl acetate. The organic layer is dried with sodium sulfate, filtered, and evaporated to dryness under vacuum. The lipid-amino acid conjugate methyl ester product is purified by silica gel column chromatography and is eluted with 1.5% methanol in methylene chloride. Other protocols can be used.

A solution of N-fatty acid or $J_2$ prostanoid-amino acid conjugate methyl ester (from ~0.6 to ~1.0 nmol,) in tetrahydrofuran (~2 to ~3 ml) is treated with 1 M aqueous lithium hydroxide (~0.5 to ~1.0 ml). The mixture is stirred for 45 minutes under nitrogen at room temperature followed by evaporation under vacuum. The residue is diluted with 10-20 ml of water, acidified to pH 3.0 with HCl and extracted with ethyl acetate. The combined extracts are washed with water, dried with sodium sulfate and evaporated under vacuum. The elmiric acid or J acid product is purified using silica gel column chromatography and eluted with methanol in methylene chloride.

Protocol #2

Figure 7:
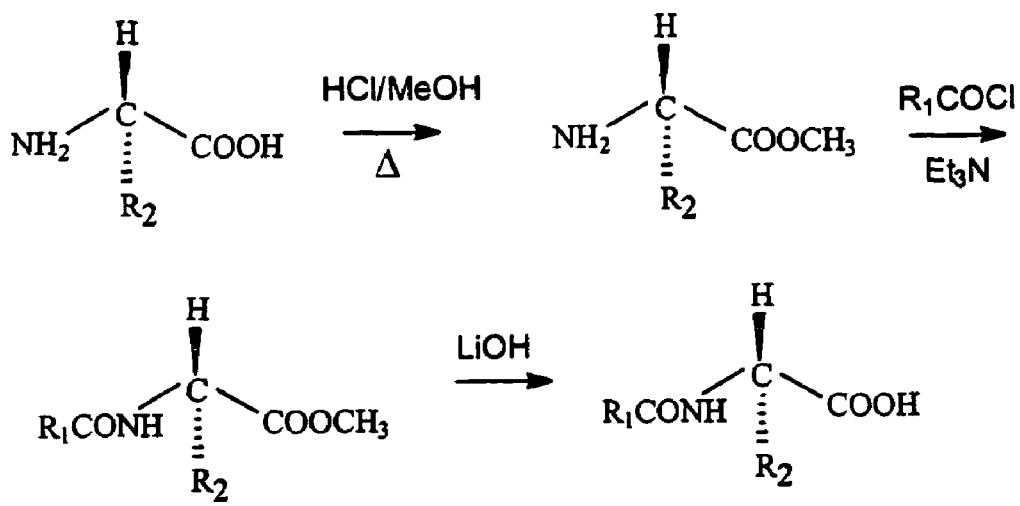
FIG. 7 is a representation of an exemplary synthesis scheme that can be used to make an elmiric acid or J acid.

The following protocol describes an alternate method of preparing a lipid-amino acid conjugate, e.g., an elmiric acid or J acid. FIG. 7 also provides a general scheme for this protocol. A fatty acid chloride or $J_2$ prostanoid chloride in methylene chloride is reacted with amino acid methyl ester in methylene chloride containing 5% triethylamine for 2-8 hours at room temperature. The mixture is then partitioned between ethyl acetate and dilute HCl, washed, dried and evaporated to an oily residue. This residue is dissolved in tetrahydrofuran and saponified by stirring under nitrogen with LiOH for 4-10 hours at room temperature. The product is diluted with water, acidified to pH 3.0 with HCl and extracted with ethyl acetate. The combined extracts are washed with water, dried with sodium sulfate, evaporated under vacuum, and purified by thin layer chromatography.

Protocol #3

Figure 8:
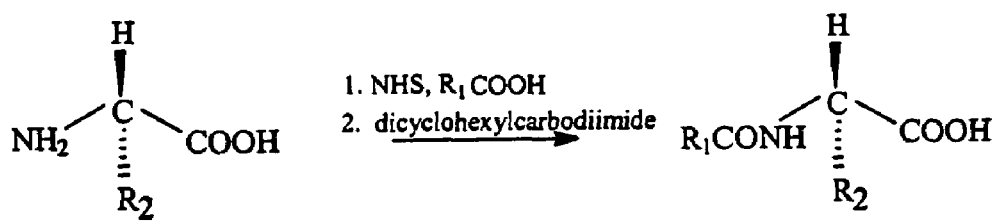
FIG. 8 is a representation of an exemplary synthesis scheme that can be used to make an elmiric acid or J acid.

The following protocol describes an alternate method of preparing a lipid-amino acid conjugate, e.g., an elmiric acid or J acid. See FIG. 8 for a general scheme of the protocol. 10-100 mg of fatty acid or $J_2$ prostanoid is added to a solution of N-hydroxysuccinimide (NHS) (4-40 mg) in 5-50 ml of ethyl acetate, followed by addition of 9-90 mg of dicyclohexylcarbodiimide. The mixture is allowed to react for 12-36 hours at room temperature, after which 10 mg of amino acid in a mixture of dioxane-KOH—NaHCO3 (2-20 ml) is added and reacted for a further 24-72 hours at 40° C. The mixture is then acidified with HCl, extracted with ethyl acetate and the product isolated by thin layer chromatography.

Methods of Use

The lipid-amino acid conjugates disclosed herein, e.g., elmiric acids and J acids, can be used as regulators of the peroxisome proliferator-activated receptor (PPAR) family member PPARγ. One or more lipid-amino acid conjugates can be screened in one of several peroxisome proliferator-activated receptor (PPAR) activation assays (as described below) to determine the PPARγ activation potency of the conjugate. One or more elmiric acids or J acids can be used to treat a disorder that involves PPARγ regulation, e.g., diabetes or a disorder of lipid metabolism and glucose homeostasis. Elmiric acids or J acids can also be co-administered to patients taking antiretroviral medications to treat lipodystrophy and insulin resistance associated with certain antiretroviral therapies.

The PPARs are transducer proteins belonging to the steroid/thyroid/retinoid receptor superfamily. Three subtypes of PPAR have been identified, designated as PPAR-alpha (PPAR-α), PPAR-beta (PPAR-β) or PPAR-delta (PPAR-δ)), and PPAR-gamma (PPAR-γ). These receptors function as activator-regulated transcription factors that control the expression of target genes by binding to their responsive DNA sequence as heterodimers with retinoid x receptor (RXR).

The PPARα subtype has been cloned from *Xenopus*, humans, mouse, and rat; the PPARβ (or PPARδ) subtype from *Xenopus*, humans, and mouse; and the PPARγ subtype from *Xenopus*, humans, and hamster. These subtypes are pharmacologically distinct and differentially activated by various agents (Yu et al., *Cell*, 67:1251-1266, 1991). The following are corresponding Genbank accession numbers: PPARα(δ) (AF246303), PPARβ (AL022721), and PPARγ (AY157024). PPARγ exists as at least two isotypes, PPARγ1 and PPARγ2. PPARγ2 is expressed selectively in adipose tissue, whereas PPARγ1 is expressed at lower levels in a variety of other rodent and human tissues (Spiegelman, *Diabetes*, 47:507-514, 1998).

PPARγ is a pharmacologically important member of the nuclear receptor superfamily (Houseknecht et al., *Domest. Anim. Endocrinol.*, 22:1-23, 2002). It plays important roles in a diverse array of biological processes including lipid metabolism, glucose homeostasis, and adipocyte differentiation. The crystal structure of the PPARγ ligand-binding domain reveals a large hydrophobic cavity for ligand binding (Uppenberg et al., *J. Biol. Chem.*, 273:31108-12, 1998; and Xu et al., *Proc. Nat'l. Acad. Sci. USA*, 98:13919-24, 2001). Indeed, PPARγ binds to a wide range of synthetic and naturally occurring substances, including the antidiabetic drugs thiazolidinediones (TZDs) (Lehmann et al., *J. Biol. Chem.*, 270:12953-6, 1995; Willson et al., *J. Med. Chem.*, 39:665-8, 1996), the synthetic tyrosine analog GW347845 (Cobb et al., *J. Med. Chem.*, 41:5055-5069, 1998), polyunsaturated fatty acids (Kliewer et al., *Proc. Nat'l. Acad. Sci. USA*, 94:4318-23, 1997), metabolites of arachidonic acid including 15-deoxy-$\Delta^{12,14}$-prostaglandin $J_2$ and other $J_2$ prostanoids (Forman et al., *Cell*, 83:803-12, 1995; Kliewer et al., *Cell*, 83:813-9, 1995), NSAIDs (Lehmann et al., *J. Biol. Chem.*, 272:3406-10, 1997), and compounds of oxidized low-density lipoprotein, such as 13-hydroxyoctadecadienoic acid (13-HODE) and 15-hydroxyeicosatraenoic acid (15-HETE) (Nagy et al., *Cell*, 93:229-40, 1998).

Several of these PPARγ ligands exhibit anti-inflammatory activity in vivo (Kawahito et al., *J. Clin. Invest.*, 106:189-97, 2000; Naito et al., *Aliment Pharmacol. Ther.*, 15:865-73, 2001), and activation of PPARγ is directly linked to anti-inflammatory (Jiang et al., *Nature*, 391:82-6, 1998), and anti-tumor processes (Patel et al., *Curr. Biol.*, 11:764-8, 2001). Accordingly, activation of PPARγ inhibits the expression of cytokines, such as interleukin (IL)-1β, tumor necrosis factor α (TNFα), and nitric oxide (NO) at both the protein and transcription levels (Jiang et al., *Nature*, 391:82-6, 1998; Ricote et al., *Nature*, 391:79-82, 1998). PPARγ is expressed in adipose tissue, skeletal muscle, adrenal gland, colonic epithelium, heart, pancreas, and liver (Mukherjee et al., *J. Biol. Chem.*, 272:8071-6, 1997; Sarraf et al., *Nat. Med.*, 4:1046-52, 1998). It is also expressed in immune system related cells such as splenocytes (Clark et al., *J. Immunol.*, 164:1364-71, 2000; Kliewer et al., *Proc. Natl. Acad. Sci. USA*, 91:7355-9, 1994), synoviocytes (Ji et al., *J. Autoimmun.*, 17:215-21, 2001; Kawahito et al., *J. Clin. Invest.*, 106:189-97, 2000; Simonin et al., *Am. J. Physiol. Cell Physiol.*, 282:C125-33, 2002), helper T cells (Clark et al., *J. Immunol.*, 164:1364-71, 2000), and activated monocytes and macrophages (Jiang et al., *Nature*, 391:82-6, 1998; Kawahito et al., *J. Clin. Invest.*, 106:189-97, 2000; Ricote et al., *Nature*, 391:79-82, 1998) suggesting that PPARγ has a direct role in modulating inflammation in addition to its role in lipid metabolism and glucose homeostasis.

PPARγ modulates the expression of genes involved in the regulation of growth and differentiation in a variety of cell types that express the receptor. PPARγ has been shown to be expressed in an adipose tissue-specific manner. Its expression is induced early during the course of differentiation of several preadipocyte cell lines. PPARγ plays a role in the adipogenic signaling cascade and also regulates the ob/leptin gene which is involved in regulating energy homeostasis.

In one aspect, the new methods and compositions can be used to treat autoimmune diseases or disorders involving PPARγ by using a PPARγ regulator that is or includes a lipid-amino acid conjugate, e.g., an N-fatty acid-amino acid conjugate or $J_2$ prostanoid-amino acid conjugate. In general, the methods involve providing an amount of a PPARγ regulator sufficient to modulate the expression of genes encoding proteins involved in autoimmune diseases, such as diabetes mellitus, inflammatory cytokines such as tumor necrosis factor-α (TNF α), or inhibition of the production of inflammatory cytokines such as IL-1α, IL-1β, IL-2, IL-6, IL-8, and TNF-α, or the inhibition of their biological activity. While the PPARγ regulator can be utilized alone, the therapy can also be administered in combination with other therapeutics such as existing naturally occurring or synthetic activators, steroidal and non-steroidal anti-inflammatory agents, existing therapies for diabetes, and agents that modulate apoptosis in pathological cells.

In one embodiment, the cells to be treated are those involved in inflammatory disorders. These include inflammatory (immune system) cells (e.g., T lymphocytes and macrophages), PPARγ expressing cells and tissues involved in the pathogenesis of inflammatory diseases, including all forms of uveitis and uveoretinitis, iritis, cyclitis, choroiditis, chorioretinitis, vitritis, keratitis and conjunctivitis, systemic autoimmune disorders (e.g., type 1 diabetes mellitus, Sjogren's syndrome, and hyperthyroidism), and collagen vascular diseases (e.g., ankylosing spondylitis, rheumatoid arthritis, lupus erythematosus, Reiter syndrome, Bechet disease, ulcerative colitis, Crohn's disease, and Wegener's granulomatosis).

In another embodiment, the cells to be treated are those involved in autoimmune disorders, such as the pancreatic β-cells of a subject with diabetes.

1. PPARγ Activation Assays

The PPARγ activation potency of a lipid-amino acid conjugate described herein can be tested in vitro using one or both of the following assays.

a) The Oil Red O assay is an adipocyte differentiation assay that can be performed as described by Mukherjee et al., *J. Biol. Chem.*, 272:8071-6, 1997. Oil Red O (1-[[4-[(dimethylphenyl)azo]dimethylphenyl]azo]-2-naphthol) is a highly lipophilic dye substance that is used extensively in histology to visualize areas rich in neutral lipids such as triglycerides and cholesteryl esters. It produces an intense red color due to its light absorbtion characteristics; $\lambda_{max}$=518 nm. PPAR-γ agonist treatment of intact cells in culture often results in an accumulation of neutral lipids that are sometimes visible by light microscopy and can be stained black with osmium tetroxide and red with Oil Red O. This has been considered as a strong indication of PPAR-γ activation (See, e.g., Lenhard et al., *Antiviral Res.*, 47:121-129, 2000; Landsberg et al., *Proc. Nat'l. Acad. Sci. USA*, 100:2456-2461, 2003; Starkey et al., *J. Clin. Endocrinol. Metab.*, 88:55-59, 2003; Tang et al., *Proc. Nat'l. Acad. Sci. USA*, 100:850-855, 2003).

Generally, the Oil Red assay involves culturing cells, such as 3T3 L1 fibroblasts (American Type Culture Collection), to confluence in DMEM media supplemented with 10% calf serum. In the assay, GW347845 is a potent PPARγ specific ligand that can be used as a positive control (Cobb et al., *J. Med. Chem.*, 41:5055-5069, 1998), while vehicle treated cells are used as a baseline control. Two days after reaching confluence cells are contacted with: (i) 1-100 μg of a lipid-amino acid conjugate with vehicle (e.g., 0.1% DMSO), (ii) GW347845 with vehicle, or (iii) vehicle alone. Treatments are administered in the presence of 10 mg/ml insulin every other day. After 3-14 days of treatment with the lipid acid-amino acid conjugate and 7 days with GW347845 at confluence, cells are fixed and stained with Oil Red O (Sigma).

Oil Red O staining is performed as follows: (1) media is removed, and 0.5 ml formalin is added to the cells, (2) after 1 hour, formalin is removed and cells are washed 2× with water, (3) 0.1 ml oil red staining solution is added for 1 hour at room temperature, (4) stained cells are washed with water, thoroughly drained, and then dried at 37° C. for 1 hour, (5) dye is extracted with 1.00 ml of isopropyl alcohol on shaker for 15 minutes, and 6) absorbance at 510 nm is measured.

b) PPARγ activation potency can also be tested using a "lipid incorporation" assay that can be performed as follows. Monolayers of cells, e.g., C6 rat glioma cells, are prepared in 24-well culture dishes. Carboxy-labeled [$^{14}$C]oleic acid (150,000 dpm/well) (obtained from American Radio Chemicals (ARC) St. Louis, Mo.; specific activity: 55 mCi/mmol) is added to each monolayer and incubated for 2 hours at 4° C. Cells are then treated with an N-fatty acid-amino acid conjugate or J$_2$ prostanoid-amino acid conjugate in vehicle, e.g., 10 μl of DMSO to 1 ml of the culture medium covering each monolayer. Treatment is continued for 48 hours except where indicated otherwise, at which time, medium is removed and discarded, since preliminary examination showed that little if any radiolabeled lipid is present. After washing with PBS (1 ml), the cellular lipids are extracted for 0.5 hour with 0.5 ml of 95% ethanol at room temperature. Treatments can be performed in quadruplicate; vehicle-treated cells serve as a control.

Prior to evaporation under vacuum, [$^{14}$C]cholesterol (50,000 dpm) (from ARC; specific activity: 50 mCi/mmol) is added as a recovery marker. The sample residues are then dissolved in 30 μl of methanol containing 10 μg each of steroyl-arachidonoyl diglyceride, triolein, and phosphatidylcholine (PC) and applied to 0.25-mm silica gel thin layer plates. A first elution is performed with dichloromethane: acetone (90:10) for the analysis of neutral lipids. The Rf values of the standards are: PC=0, cholesterol=0.38, Diacylglyceride (DG)=0.64, and Triacylglyceride (TG)=0.81. Following the quantitation of the neutral lipids, a second elution is carried out using chloroform:methanol:acetic acid:water (50:25:8:2) as the eluent for the analysis of phospholipid. The Rf value of PC is 0.33; DG and TG moved to the solvent front. All standards can be detected by exposure to iodine vapor.

Zones of radioactivity are detected by exposure of TLC plates to x-ray film for 48 hours. A computerized image of the film can be generated using the FLUOR-S™ System (Bio-Rad). Radioactivity on the chromatograms can be quantified using NIH Image software. Peak height values of the display are used since the zones all showed narrow sharp peaks. These are adjusted for recovery using the individual cholesterol standard values for each zone. The values obtained are then divided by the numbers of cells in each well, and the results are expressed as an index/million cells.

2. Use of Lipid-Amino Acid Conjugates to Treat Diabetes

Some lipid-amino acid conjugates, e.g., elmiric acids and J acids, can reduce blood glucose and triglyceride levels and are accordingly useful for the treatment of disorders such as diabetes and obesity.

In one embodiment, one or more elmiric acids or J acids are used to regulate PPARγ in a treatment for an autoimmune disorder such as diabetes. Diabetes is a multifactorial disease that occurs through the failure and/or destruction of the pancreatic β-cell. There is a large body of evidence in support of the idea that inflammatory cytokines have cytotoxic effects on islet β-cells (Rabinovitch, *J. Clin. Endocrinol. Metab.*, 71:152-6, 1990) and that this cytotoxi city plays a part in β-cell destruction in insulin-dependent diabetes mellitus (IDDM).

Obesity-linked non-insulin-dependent diabetes mellitus (NIDDM) is preceded by years of insulin resistance, during which normal blood glucose levels are maintained through effective compensation by pancreatic β-cells. In approximately 20% of obese individuals, the compensation wanes, hyperglycemia appears, and overt NIDDM is diagnosed. The depressed β-cell function is thought to be due to excess free fatty acids released from adipocytes in obesity (Campbell et al., *Am. J. Physiol.*, 266:E600-5., 1994; DeFronzo, *Diabetes Metab. Rev.*, 4:727-47, 1988) acting to initially stimulate, but ultimately impair, the function of β-cells, and thus limit their compensatory capability. Thus, impaired β-cell function is a characteristic of both IDDM and NIDDM.

Elmiric acids and J acids are useful for the modification, treatment, and/or prophylaxis of insulin resistance (Type II diabetes), impaired glucose tolerance, dyslipidemia, disorders related to Syndrome X such as hypertension, obesity, insulin resistance, hyperglycemia, atherosclerosis, hyperlipidemia, coronary artery disease, and other cardiovascular disorders associated with diabetes. Other disorders associated with diabetes include the anti-apoptotic effect of PPARγ regulators that serves to protect cells from premature death and promote their survival, as in degenerative and dystrophic diseases, e.g., retinal neural and glial cells in diabetic retinopathy and both "wet" (exudative) and "dry" (aereolar) age-related macular degeneration.

Before administration to a subject, an elmiric acid or J acid can be tested for biological activity (i.e., ability to decrease cell proliferation) both in vitro or in vivo. In vitro testing can be performed as described in the examples described herein. In vivo animal models for diabetes are also well known in the art, for example, obese mice (ob/ob), and diabetic (db/db) mice from the Jackson Laboratories (Bar Harbor, Me.) (see, e.g., Collins et al., *J. Biol. Chem.*, 271:9437-9440, 1996; Darling, *Curr. Opin. Genet. Dev.*, 6:289-294, 1996; Andersson, *Ann. Med.*, 28:5-7, 1996; Van Heek et al., *J. Clin. Invest.*, 99:385-390, 1997). These animal models can be used to assess the effect of the N-fatty acid-amino acid conjugate or J$_2$ prostanoid-amino acid conjugate on diabetes and obesity.

3. Use of Lipid-Amino Acid Conjugates to Treat Lipid Metabolism and Glucose Homeostasis Disorders In another embodiment, one or more lipid-amino acid conjugates, e.g., elmiric acids or J acids, are administered to a subject to regulate PPARγ and thereby treat or modify a disorder related to lipid metabolism and glucose homeostasis.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialized proteins are induced during adipocyte differentiation, most of them being involved in lipid storage and metabolism. Accordingly, some elmiric acids and J acids that regulate PPARγ can be used to regulate lipid metabolism and glucose homeostasis by regulating adipocyte tissue differentiation.

The exact link from activation of PPARγ to changes in glucose metabolism, most notably a decrease in insulin resistance in muscle, has not yet been clarified. While not intending to be bound by theory, a possible link is via free fatty acids. Activation of PPARγ induces lipoprotein lipase (LPL), fatty acid transport protein (FATP) and acyl-coA synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence. PPARγ is involved in stimulating β-oxidation of fatty acids. Accordingly, some conjugates that regulate PPARγ can be used to regulate insulin resistance by regulating fatty acid concentration in plasma.

4. Use of Lipid-Amino Acid Conjugates to Treat Inflammation Involving PPARγ

In another embodiment, one or more lipid-amino acid conjugates, e.g., elmiric acids or J acids, that activate PPARγ activity can be used to treat disorders related to undesirable inflammatory responses that are inhibited by PPARγ activation. Thus, an elmiric acid or J acid can be used for the treatment of diseases including, but not limited to, immunologically-mediated inflammatory diseases such as rheumatoid arthritis, systemic lupus erythematosus, psoriasis, eczema, multiple sclerosis, diabetes, and thyroiditis. In addition, the present compounds can modulate bone formation/resorption and are useful in the treatment of conditions including, but not limited to, ankylosing spondylitis, gout, arthritis associated with gout, osteoarthritis, and osteoporosis.

Psoriasis is a chronic skin disease of scaling and inflammation. Psoriasis occurs when skin cells quickly rise from their origin below the surface of the skin and pile up on the surface before they have a chance to mature. Typically this movement (also called turnover) takes about a month, but in psoriasis it may occur in only a few days. In its typical form, psoriasis results in patches of thick, inflamed skin covered with silvery scales. These patches, which are sometimes referred to as plaques, usually itch or feel sore. They most often occur on the elbows, knees, other parts of the legs, scalp, lower back, face, palms, and soles of the feet, but they can occur on skin anywhere on the body. Diagnosis of psoriasis is based primarily on these characteristic symptoms. A skin biopsy can be useful in diagnosis. Psoriatic arthritis occurs in some patients with psoriasis and can often affect the joints at the ends of the fingers and toes. Back pain may occur if the spine is involved. Lipid-amino acid conjugates that activate PPARγ activity can be useful in treating, preventing, or alleviating psoriasis or one or more symptoms of psoriasis or psoriatic arthritis, e.g., in topical pharmaceutical compositions.

Rheumatoid arthritis is an autoimmune inflammatory disease that causes pain, swelling, stiffness, and loss of function in the joints. Rheumatoid arthritis often presents in a symmetrical pattern. The disease can affect the wrist and finger joints closest to the hand, as well as other parts of the body. In addition, patients with rheumatoid arthritis may have fatigue, occasional fevers, and a general malaise. Positive factors for diagnosis of rheumatoid arthritis include the "rheumatoid factor" blood antibody and citrulline antibody. Lipid-amino acid conjugates that activate PPARγ activity can be useful in treating, preventing, or alleviating rheumatoid arthritis or one or more symptoms of rheumatoid arthritis, e.g., in topical or systemic pharmaceutical compositions.

5. Use of Lipid-Amino Acid Conjugates in Antiretroviral Therapies

In still another embodiment, one or more lipid-amino acid conjugates, e.g., elmiric acids or J acids, are used in conjunction with antiretroviral therapies, e.g., anti-HIV therapies. The increased use of potent antiretroviral therapies, such as the protease inhibitor cocktails administered to patients infected with HIV, has led to an increase in the complications associated with antiretroviral therapies. Complications include insulin resistance and lipodystrophy.

Lipodystrophy involves adverse changes in lipid metabolism and fat redistribution. Small molecules that activate PPARγ have been administered to patients with congenital lipodystrophy, and these molecules reportedly stimulated adipogenesis and improved insulin sensitivity. See, Arioglu et al., *Ann. Intern. Med.*, 133:263-74, 2000. On this basis, PPARγ activators such as fibrates and thiazolidinediones are also being studied as adjuvants for HIV protease inhibitor drugs to reduce associated complications, such as lipodystrophy and insulin resistance, see, e.g., Hadigan et al., *Ann Intern Med.*, 140:786-794, 2004.

Lipid-amino acid conjugates that activate PPARγ can therefore be administered as adjuvants to antiretroviral therapies to reduce associated complications. For example, an effective dose of one or more elmiric acids or J acids can be co-administered with anti-HIV protease inhibitor cocktail to patients in need of anti-HIV treatment. Co-administration of elmiric acids or J acids can suppress side effects associated with anti-HIV treatments, such as lipodystrophy and insulin resistance.

Pharmaceutical Compositions

Pharmaceutical compositions containing one or more lipid-amino acid conjugates, e.g., elmiric acids or J acids, may be prepared by conventional techniques (e.g., as described in Remington: The Science and Practise of Pharmacy, 19th Ed., 1995). The compositions may appear in conventional forms, such as capsules, tablets, aerosols, solutions, suspensions, or topical applications.

Typical compositions include an elmiric acid or J acid associated with a pharmaceutically acceptable excipient which may be a carrier or a diluent or be diluted by a carrier, or enclosed within a carrier which can be in the form of a capsule, sachet, paper, or other container. In making the compositions, conventional techniques for the preparation of pharmaceutical compositions may be used. For example, the compound of interest will typically be mixed with a carrier, or diluted by a carrier, or enclosed within a carrier, which may be in the form of an ampule, capsule, sachet, paper, or other container. When the carrier serves as a diluent, it may be solid, semi-solid, or liquid material, which acts as a vehicle, excipient, or medium for the active compound. The compound of interest can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

The route of administration may be any route that effectively transports the lipid-amino acid conjugate to the appropriate or desired site of action, such as oral, nasal, pulmonary, transdermal, or parenteral, e.g., rectal, depot, subcutaneous, intravenous, intraurethral, intramuscular, intranasal, ophthalmic solution or an ointment, typically the oral route.

For nasal administration, the preparation may contain the elmiric acid or J acid dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabens.

To prepare topical formulations, the elmiric acid or J acid is mixed into a dermatological vehicle as is known in the art. Such topical pharmaceutical compositions can exist in many forms, e.g., in the form of a solution, cream, ointment, gel, lotion, shampoo, or aerosol formulation adapted for application to the skin. The weight percent of the active ingredient in the composition useful in the methods described herein typically ranges from 0.01% to 10%, e.g., 0.01% to 1%, 0.1% to 10%, 0.01% to 1%, 1% to 5%, or 5% to 10% (based on the total weight of the composition) in admixture with a pharmaceutically acceptable carrier. A wide variety of carrier materials can be employed in the compositions described herein such as alcohols, aloe vera gel, allantoin, glycerine, vitamin A and E oils, mineral oils, and polyethylene glycols. The compositions can include dimethylsulfoxide (DMSO) or other permeabilizing agents. Other additives, e.g., preservatives, fragrance, sunscreen, or other cosmetic ingredients, can be present in the composition.

For ophthalmic applications, the elmiric acid or J acid is formulated into solutions, suspensions, and ointments appropriate for use in the eye. The concentrations are usually as discussed above for local preparations. For ophthalmic formulations (see Mitra (ed.), Ophthalmic Drug Delivery Systems, Marcel Dekker, Inc., New York, N.Y., 1993 and also Havener, W. H., Ocular Pharmacology, C.V. Mosby Co., St. Louis, 1983).

For oral administration, either solid or fluid unit dosage forms can be prepared. For preparing solid compositions such as tablets, an elmiric acid or J acid is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers.

Capsules are prepared by mixing the elmiric acid or J acid with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill, such as the use of suitable injectable solutions or suspensions. The formulation, which is sterile, is suitable for various topical or parenteral routes including intra-dermal, intramuscular, intravascular, and subcutaneous.

In addition to the elmiric acid or J acid, the compositions may include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or non-toxic, non-therapeutic, non-immunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives, and excipients are those amounts which are effective to obtain a pharmaceutically acceptable formulation in terms of solubility, biological activity, etc.

The elmiric acid or J acid may be incorporated into microspheres. The compound of interest can be loaded into albumin microspheres that can be used as a dry powder for nasal administration. Other materials suitable for the preparation of microspheres include agar, alginate, chitosan, starch, hydroxyethyl starch, ovalbumin, agarose, dextran, hyaluronic acid, gelatin, collagen, and casein. The microspheres can be produced by various processes known to the person skilled in the art such as a spray drying process or an emulsification process. Microspheres are typically less than 500 μm in diameter, e.g., less than 200, 100, 50, 20, 10, 5, 1, 0.5, 0.1, 0.05, or 0.01 μm. Microspheres can be used in multiple methods of delivering lipid-amino acid conjugates, including topical and transdermal delivery.

For example, albumin microspheres can be prepared by adding rabbit serum albumin in phosphate buffer to olive oil with stirring to produce a water in oil emulsion. Glutaraldehyde solution is then added to the emulsion and the emulsion stirred to cross-link the albumin. The microspheres can then be isolated by centrifugation, the oil removed and the spheres washed, e.g., with petroleum ether followed by ethanol. Finally, the microspheres can be sieved and collected and dried by filtration.

Starch microspheres can be prepared by adding a warm aqueous starch solution, e.g., of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurried in a solvent such as ethanol, after which the particles are again filtered off and laid to dry in air.

The microspheres can be hardened by well known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative.

The term "unit dosage form" refers to physically discrete units suitable as unitary dosages for subjects, e.g., human subjects or mammalian subjects, e.g., dogs, cats, and rodents, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions can be included in kits, which can contain one or more unit dosage forms of the composition and instructions for use to treat one or more of the disorders described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

An effective quantity of an elmiric acid or J acid is employed in treatment. The dosage of compounds used in accordance with the invention varies depending on the compound and the condition being treated. For example, the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer. Exemplary dosages of lipid-amino acid conjugates are 0.1 to 50 mg/kg, e.g., 0.1 to 20 mg/kg, 0.5 to 50 mg/kg, 0.1 to 2.0 mg/kg, 2.0 to 10 mg/kg, or 10 to 50 mg/kg body weight of the patient.

Elmiric acids and J acids can also be given orally in combination with natural or synthetic compounds that bind to or modify the activity of the vitamin D receptor or in combination with compounds that bind to or modify the activity of the retinoid X receptor to provide for a synergistic effect in the treatment or prevention of the disorders. Examples of such compounds that provide for synergistic effect when given in combination with the drugs encompassed by the current invention include vitamin D analogs, various retinoic acid derivatives, and other activators for retinoid X receptors or retinoic acid receptors including, but not limited to, compounds such as LG 100268, tazarotene, TTNPB, AGN 190121, adapalene, or LGD1069 (TARGRETIN™).

EXAMPLES

The invention will be further described in the following examples, which do not limit the scope of the invention described in the claims.

Example 1

Synthesis of Arachidonoyl-D-Alanine

N-fatty acid-D-alanine conjugate was prepared from chirally pure D-amino acid methyl ester (Aldrich Chemicals). Arachidonoyl chloride (Nucheck) in methylene chloride was reacted with alanine methyl ester in methylene chloride containing 5% triethylamine for 4 hours at room temperature. The mixture was partitioned between ethyl acetate and dilute HCl, washed, dried and evaporated to an oily residue. This residue was dissolved in tetrahydrofuran and saponified by stirring under nitrogen with 1 N LiOH for 5 hours at room temperature. The product was extracted as above and subjected to thin layer chromatography. The principal product was identified as N-arachidonoyl-D-alanine by mass spectrometric analysis and exhibited an $MH^+$ of 376.1. Circular dichroism measurements showed mirror image spectra between 220 and 240 nm when compared to the L isomer. The [α]values were $-16.6 \times 10^5$ for the D isomer and $+16.5 \times 10^5$ for the L isomer.

Example 2

Synthesis of Other Elmiric Acids

The synthesis procedure of Example 1 was used to prepare the arachidonyl and palmityl conjugates with 1-amino-cyclohexane carboxylic acid, 1-amino-cyclopentane carboxylic acid, and 2-amino-isobutyric acid. The synthesized compounds were N-palmitoyl-1-amino cyclohexane-COOH, N-palmitoyl-1 amino-cyclopentane-COOH, N-palmitoyl-2-amino-isobutyric acid, N-arachidonoyl-1-amino-cyclohexane-COOH, and N-arachidonoyl-1-amino-cyclopentane-COOH, and N-arachidonoyl-2-amino-isobutyric acid.

Example 3

Synthesis of Other Elmiric Acids

A solution of 10 mg arachidonic acid (5Z, 8Z, 11Z, 14Z-eicosatetraenoic-5, 6, 8, 9, 11, 12, 14, 15 acid) is added to a solution of N-hydroxysuccinimide (NHS) (4 mg) in 5 ml of ethyl acetate, followed by the addition of 9 mg of dicyclohexylcarbodiimide (CDI) to the solution. The mixture is allowed to react for 24 hours at room temperature, followed by the addition of 10 mg of amino acid in a mixture of dioxane-KOH—NaHCO$_3$ (2 ml). The resulting mixture is reacted for an additional 48 hours at 4° C. The mixture is then acidified with HCl, extracted with ethyl acetate, and the N-arachidonoyl-amino acid product is isolated by thin layer chromatography (acetonitrile, 96; water, 4). The identity is confirmed by NMR and mass spectral analysis.

Example 4

Synthesis of J Acids

A solution of 10 mg 15-deoxy-$\Delta^{12,14}$-prostaglandin J$_2$ is added to a solution of N-hydroxysuccinimide (NHS) (4 mg) in 5 ml of ethyl acetate, followed by the addition of 9 mg of dicyclohexylcarbodiimide (CDI) to the solution. The mixture is allowed to react for 24 hours at room temperature, followed by the addition of 10 mg of amino acid in a mixture of dioxane-KOH—NaHCO$_3$ (2 ml). The resulting mixture is reacted for an additional 48 hours at 4° C. The mixture is then acidified with HCl, extracted with ethyl acetate, and the N-15-deoxy-$\Delta^{12,14}$-prostaglandin J$_2$-amino acid product is isolated by thin layer chromatography (acetonitrile, 96: water, 4). The identity is confirmed by NMR and mass spectral analysis.

Example 5

Testing of Lipid-Amino Acid Conjugates

N-arachidonoyl-D-alanine is subjected to the Oil Red O assay, discussed in more detail supra. In the assay, 3T3 L1 fibroblasts are cultured in DMEM supplemented with 10% calf serum. Two days after confluence, cells are treated with 0.1% DMSO (vehicle), 20-100 µM N-arachidonoyl-D-alanine in vehicle, or 1 µM GW347845 (Cobb et al., *J. Med. Chem.*, 41:5055-5069, 1998) in vehicle. Each of the three treatments is administered to the cells with 10 µg/ml of insulin. After seven days of treatment with GW347845 and 10-14 days of treatment with N-arachidonoyl-D-alanine, cells are fixed and stained with Oil Red O. Red staining indicates lipid droplets in the cytoplasm.

RT-PCR analysis of expressed genes is performed as a secondary test of adipocyte differentiation. Messenger RNA from fibroblasts is harvested and RT-PCR is performed to amplify adipocyte specific transcripts, e.g., PPARγ2 and aP2, or the transcript of a ubiquitous housekeeping gene, e.g., GAPDH. PCR products are analyzed on 1% agarose gel and stained with ethidium bromide. PPARγ2 and aP2 are induced significantly after treatment with 1 µM GW347845 or after treatment with 20-100 µM N-arachidonoyl-D-alanine relative to vehicle-treated cells. Expression of the housekeeping gene GAPDH is assayed to ensure equal expression in all samples.

Example 5

In Vivo Testing of Lipid-Amino Acid Conjugates

Paw Edema

Suppression of chemically induced paw edema in mice is a long-standing assay for assessment of an agent's potential anti-inflammatory activity. A lipid-amino acid conjugate, e.g., an elmiric acid or a J acid, is tested in this model for inhibitory effects on chemically induced edema.

Platelet activating factor (PAF) (1 µg) or arachidonic acid (1 mg) dissolved in 50 µl of 5% ethanol in saline is injected subcutaneously in the right hind paw of an anesthetized mouse. Paw volume is measured by water displacement before treatment and 15 minutes after PAF injection or 30 minutes after arachidonate injection. Lipid-amino acid conjugates or control compounds are given by gavage in safflower oil 90 minutes before edema induction.

Animals are administered lipid-amino acid conjugates at doses of 0.1, 0.5, 1.0, 5.0, 25, and 50 mg/kg or vehicle (0.05 ml safflower oil) by gavage essentially as described (Burstein et al., *J. Med. Chem.*, 35:3135-3141, 1992). Ten male CD-1 mice are used in each group. Controls are vehicle, indomethacin at 2.0 mg/kg, and ajulemic acid at 1.0 mg/kg. ED-50 values are obtained and compared with control values. Paw volume changes are compared using a paired t-test. Lipid-amino acid conjugates that reduce paw volume changes by 50% are candidate anti-inflammatory agents.

Subcutaneous Air Pouch

The subcutaneous air pouch simulates a synovial lined joint space by providing a blind connective tissue cavity without a mesothelial basement membrane; the pouch lining has the two cell types (fibroblasts and macrophage-like cells) common to synovia. The pouch provides a way to induce and monitor the effect of a lipid-amino acid conjugate, e.g., an elmiric acid or a J acid, on an inflammatory response. The response to IL-1β and TNFα is typical of an acute inflammatory reaction, with polymorphonuclear leukocyte infiltration of the pouch wall and cavity increasing in a dose-dependent manner.

Pouches are established on the backs of female Swiss (CD-1) mice by subcutaneous injection of 5 ml of air on three consecutive days. After 6 days, animals (10 per group) are treated with the appropriate agent, a lipid-amino acid conjugate or control, for 3 days (see below). Inflammation is induced on day 3 of treatment by injection into the pouch cavity of 10 ng rhuIL-1β plus 0.25 ng rHuTNFα in 3 ml of 1% carboxymethylcellulose. Inflammation is quantified 6 hours later by determination of pouch exudate volume and leukocyte count.

Animals are administered analogs at doses of 0.1, 0.5, 1.0, 5.0, 25, and 50 mg/kg or vehicle (0.05 ml safflower oil) by gavage as described (Zurier et al., *Arthritis Rheum.*, 41: 163-170, 1998). Controls are vehicle, indomethacin at 2.0 mg/kg, and ajulemic acid at 1.0 mg/kg. ED-50 values are obtained and compared with control values by ANOVA. Lipid-amino acid conjugates that reduce pouch exudate volume or leukocyte count by 50% are candidate anti-inflammatory agents.

Adjuvant Induced Arthritis Model of Chronic Inflammation and Tissue Injury

The polyarthritis model of adjuvant disease in the rat has been used extensively for evaluating anti-inflammatory and immunosuppressive drugs. This model can be used to test the effect of a lipid-amino acid conjugate, e.g., an elmiric acid or J acid, on the severity of the inflammatory response.

Chronic polyarthritis is induced in male Lewis rats (initial weight 125 gm) by intradermal injection of Freund's complete adjuvant (2 mg *Mycobacterium butyricum* in 0.1 ml mineral oil) at the tail base (N=8). Animals are anesthetized with sodium pentobarbital during the procedure. Arthritis in all 4 paws is assessed visually, and each paw is scored clinically for degree of inflammation using a 0-4 scale (0=normal; 1=redness; 2=redness, pain, slight swelling; 3=redness, severe pain, severe swelling; 4=ankylosis). An examiner who has no knowledge of the treatment groups into which rats have been placed evaluates paws. Rats are handled gently, and those with severe arthritis and extreme pain are sacrificed. Weight change and activity are also recorded over the course of the experiment.

Animals are either untreated, treated with safflower oil, or treated with the lipid amino acid conjugates or controls in a volume of 90-120 µl (adjusted for animal weight) each day, beginning on day 3 after adjuvant injection. Compounds are administered with a 5 cm gavage needle. Joints are evaluated every other day. Animals are sacrificed on day 35, and hind limbs are then removed for histomorphologic examination. A dose range of 0.1, 0.5, 1.0, 5.0, 25, and 50 mg/kg of lipid-amino acid conjugate administered thrice weekly is utilized. AJA (1.0 mg/kg) and indomethacin (2.0 mg/kg) serve as controls.

Hind limbs of animals are fixed in 10% buffered formalin and then decalcified in 10% formic acid. Several sections of each tibiotarsal joint are stained with hematoxylin and eosin. Individual sections are studied without knowledge of the treatment groups into which animals are placed. Lipid-amino acid conjugates that reduce inflammation score by 50% are candidate anti-inflammatory agents.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified compound having the following general formula (Formula I):

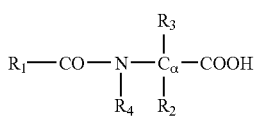

(I)

wherein $R_1$ is a hydrocarbon chain of a fatty acid selected from the group consisting of myristic acid, palmitic acid, stearic acid, oleic acid, linoleic acid, linolenic acid, eicosatrienoic acid, arachidonic acid, eicosapentenoic acid, and docosatetraenoic acid; and wherein (a) $R_3$ and $R_4$ are hydrogens, and $R_2$ is a side chain of a phenyl-glycine or a phenyl-glycine derivative;

(b) $R_3$ and $R_4$ are hydrogens, and $R_2$ is a side chain of a phenyl-alanine derivative having the following general formula (Formula IV):

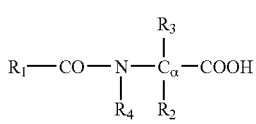

(I)

wherein X, Y, and Z, are independently H, $OCH_3$, F, Cl, I, $CH_3$, $C_2H_5$, $i-C_3H_7$, $NH-CO-CH_3$, SH, $NH_2$, CN, $CH_2NH_2$, COOH, CHO, $NO_2$, $CONH_2$, $COCH_3$, or $CH_2OH$, or wherein X is H, Y is OH, and Z is H, or wherein X is H, Y is H, and Z is OH;

(c) $R_3$ is a hydrogen, and $R_2$ and $R_4$, together, form a side chain of a proline derivative of Formula V, VI, or VII:

(V)

(VI)

(VII)

wherein the arrow denotes $C_\alpha$ of formula I, and wherein X is CN, CHO, $CH_2OH$, $CH_2NH_2$, COOH, $CH_2CN$, $NH_2$, or phenyl; or (d) $R_3$ and $R_4$ are hydrogens, and $R_2$ is a side chain of an amino acid selected from the group consisting of serine, threonine, methionine, tyrosine, lysine, aspartic acid, and glutamic acid, and the $C\alpha$ has the same stereochemistry as a D amino acid.

2. The compound of claim 1, wherein the fatty acid is arachidonic acid.

3. A purified compound having the following general formula (Formula I):

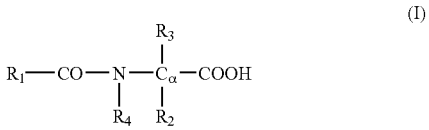

(I)

wherein $R_1$ is a hydrocarbon chain of a non-mammalian fatty acid or a non-carboxyl portion of a $J_2$ prostanoid selected from the group consisting of pentadecanoic acid; heptadecanoic acid; nonadecanoic acid; heneicosanoic acid; 9-trans-tetradecanoic acid, 14:1T; 10-trans-pentadecanoic acid, 15:1T; 9-trans-hexadecenoic acid, 16:1T; 10-heptadecenoic acid, 17:1; 10-trans-heptadecenoic acid, 17:1T; 7-trans-nonadecenoic acid, 19:1T; 10,13-nonadecadienoic acid, 19:2; 11-trans-eicosenoic acid, 20:1T; 12-heneicosenoic acid, 21:1; prostaglandin $J_2$; 15-deoxy-$\Delta^{12,14}$-prostaglandin $J_2$; $\Delta^{12}$-prostaglandin $J_2$; and 9,10-dihydro-15-deoxy-$\Delta^{12,14}$-prostaglandin $J_2$; and wherein (a) $R_3$ and $R_4$ are hydrogens, and $R_2$ is a side chain of a phenyl-glycine or a phenyl-glycine derivative;

(b) $R_3$ and $R_4$ are hydrogens, and $R_2$ is a side chain of a phenyl-alanine derivative;

(c) $R_3$ is a hydrogen, and $R_2$ and $R_4$ together form a side chain of a proline derivative of Formula V, VI, or VII:

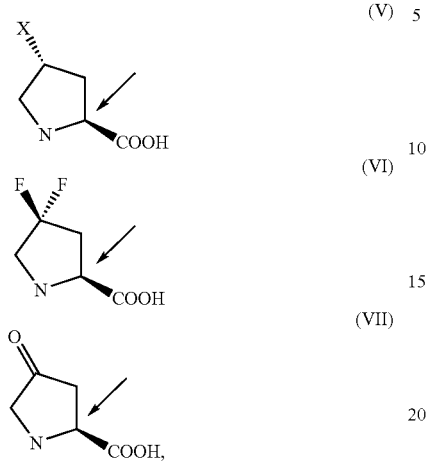

wherein the arrow denotes $C_\alpha$ of formula I, and wherein X is CN, CHO, $CH_2OH$, $CH_2NH_2$, COOH, $CH_2CN$, $NH_2$, or phenyl; or (d) $R_3$ and $R_4$ are hydrogens, and $R_2$ is a side chain of an amino acid selected from the group consisting of glycine, alanine, valine, leucine, isoleucine, seine, threonine, methionine, phenylalanine, tyrosine, lysine, aspartic acid, glutamic acid, asparagine, and glutamine.

4. A purified compound having the following general formula (Formula II):

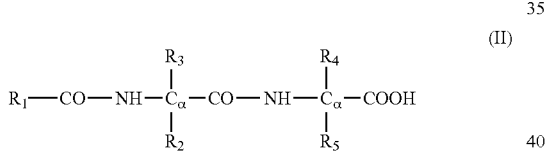

wherein $R_1$ is a non-carboxyl portion of a $J_2$ prostanoid selected from the group consisting of prostaglandin $J_2$, 15-deoxy-$\Delta^{12,14}$-prostaglandin $J_2$, $\Delta^{12}$-prostaglandin $J_2$, and 9,10-dihydro-15-deoxy-$\Delta^{12,14}$-prostaglandin $J_2$, wherein $R_2$ and $R_3$ are substituents of a natural amino acid or an amino acid analog, and wherein $R_4$ and $R_5$ are substituents of a natural amino acid or an amino acid analog, such that the compound consists of a lipid acid amide linked to a dipeptide, wherein if $R_2$ and $R_3$ are substituents of an amino acid analog, $R_2$ and $R_3$ are substituents of an amino acid analog selected from the group consisting of 1-amino-cyclopropane carboxylic acid, 1-amino-cyclopentane carboxylic acid, 1-amino-cyclohexane carboxylic acid, 2-aminoisobutyric acid, phenyl-glycine, a phenyl-glycine derivative, a phenylalanine derivative, and a D amino acid; and if $R_4$ and $R_5$ are substituents of an amino acid analog, $R_4$ and $R_5$ are substituents of an amino acid analog selected from the group consisting of 1-amino-cyclopropane carboxylic acid, 1-amino-cyclopentane carboxylic acid, 1-amino-cyclohexane carboxylic acid, 2-aminoisobutyric acid, phenyl-glycine, a phenyl-glycine derivative, a phenyl-alanine derivative, and a D amino acid.

5. A pharmaceutical composition comprising the compound of claim 1.

6. A pharmaceutical composition comprising the compound of claim 2.

7. A pharmaceutical composition comprising the compound of claim 3.

8. A pharmaceutical composition comprising the compound of claim 4.

9. A purified compound having the following general formula (Formula I):

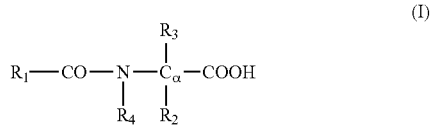

wherein $R_1$ is a hydrocarbon chain of a fatty acid selected from the group consisting of: myristic acid, palmitic acid, stearic acid, oleic acid, linoleic acid, linolenic acid, eicosatrienoic acid, arachidonic acid, eicosapentenoic acid, and docosatetraenoic acid; pentadecanoic acid; heptadecanoic acid; nonadecanoic acid; heneicosanoic acid; 9-trans-tetradecanoic acid, 14:1T; 10-trans-pentadecanoic acid, 15:1T; 9-trans-hexadecenoic acid, 16:1T; 10-heptadecenoic acid, 17:1; 10-trans-heptadecenoic acid, 17:1T; 7-trans-nonadecenoic acid, 19:1T; 10,13-nonadecadienoic acid, 19:2; 11-trans-eicosenoic acid, 20:1T; 12-heneicosenoic acid, 21:1; or wherein $R_1$ is the non-carboxyl portion of a $J_2$ prostanoid selected from the group consisting of prostaglandin $J_2$; 15-deoxy-$\Delta^{12,14}$-prostaglandin $J_2$; $\Delta^{12}$-prostaglandin $J_2$; and 9,10-dihydro-15-deoxy-$\Delta^{12,14}$-prostaglandin $J_2$; and wherein (a) $R_4$ is a hydrogen, and $R_2$ and $R_3$ together form a cyclic side chain of an amino acid analog selected from the group consisting of 1-amino-cyclopropane carboxylic acid, 1-amino-cyclopentane carboxylic acid, and 1-amino-cyclohexane carboxylic acid; or (b) $R_4$ is a hydrogen, and $R_2$ and $R_3$ are two methyl groups of 2-aminoisobutyric acid.

10. The compound of claim 9, wherein the compound is selected from the group consisting of:
N-arachidonoyl-1-amino-cyclohexane-COOH;
N-arachidonoyl-1-amino-cyclopentane-COOH;
N-arachidonoyl-2-amino-isobutyric acid;
N-palmitoyl-1-amino cyclohexane-COOH;
N-palmitoyl-1amino-cyclopentane-COOH; and
N-palmitoyl-2-amino-isobutyric acid.

11. The compound of claim 10, wherein the compound is N-arachidonoyl-2-amino-isobutyric acid.

12. A pharmaceutical composition comprising the compound of claim 10.

13. A pharmaceutical composition comprising the compound of claim 11.

14. A pharmaceutical composition comprising the compound of claim 9.

15. The compound of claim 4, wherein $R_2$ and $R_3$ together and $R_4$ and $R_5$ together are each substituents of an amino acid analog independently selected from the group consisting of 1-amino-cyclopropane carboxylic acid, 1-amino-cyclopentane carboxylic acid, 1-amino-cyclohexane carboxylic acid, 2-aminoisobutyric acid, phenyl-glycine, a phenyl-glycine derivative, a phenyl-alanine derivative, and a D amino acid.

16. The compound of claim 3, wherein $R_1$ is a non-carboxyl portion of a $J_2$ prostanoid selected from the group consisting of is prostaglandin $J_2$; 15-deoxy-$\Delta^{12,14}$-prostaglandin $J_2$; $\Delta^{12}$-prostaglandin $J_2$; and 9,10-dihydro-15-deoxy-$\Delta^{12,14}$-prostaglandin $J_2$.

17. The compound of claim 9, wherein $R_1$ is the non-carboxyl portion of a $J_2$ prostanoid selected from the group consisting of prostaglandin $J_2$; 15-deoxy-$\Delta^{12,14}$-prostaglandin $J_2$; $\Delta^{12}$-prostaglandin $J_2$; and 9,10-dihydro-15-deoxy-$\Delta^{12,14}$-prostaglandin $J_2$.

* * * * *

UNITED STATES PATENT AND TRADEMARK OFFICE
CERTIFICATE OF CORRECTION

PATENT NO. : 7,544,714 B2  Page 1 of 1
APPLICATION NO. : 11/183055
DATED : June 9, 2009
INVENTOR(S) : Sumner H. Burstein and Robert B. Zurier It is certified that error appears in the above-identified patent and that said Letters Patent is hereby corrected as shown below:

Title page, item (56), column 2, line 33, replace "15-deoxy$\Delta^{12,14}$" with --15-deoxy-$\Delta^{12,14}$--; lines 39-40, replace "15deoxy$\Delta^{12,14}$PGJ$_2$" with --15-deoxy-$\Delta^{12,14}$ PGJ$_2$--.

Column 25, lines 59 to 64, the formula should appear as follows:

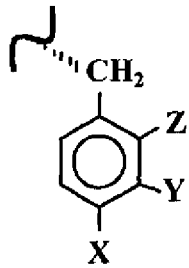

Column 26, line 34, replace "C$\alpha$" with --C$_\alpha$--.

Column 27, line 29, replace "seine" with --serine--.

Column 28, line 48, replace "1amino" with --1-amino--.

Column 29, line 1, after "of" delete "is".

Signed and Sealed this

Eighteenth Day of August, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,544,714 B2 | Page 1 of 1 |
| APPLICATION NO. | : 11/183055 | |
| DATED | : June 9, 2009 | |
| INVENTOR(S) | : Burstein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 344 days.

Signed and Sealed this

Second Day of November, 2010

David J. Kappos
*Director of the United States Patent and Trademark Office*